(12) United States Patent
Takagi et al.

(10) Patent No.: US 10,568,609 B2
(45) Date of Patent: Feb. 25, 2020

(54) ULTRASOUND IMAGE PROCESSING METHOD AND ULTRASOUND DIAGNOSTIC DEVICE USING ULTRASOUND IMAGE PROCESSING METHOD

(71) Applicant: KONICA MINOLTA, INC., Chiyoda-ku, Tokyo (JP)

(72) Inventors: Kazuya Takagi, Machida (JP); Yoshihiro Takeda, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 1223 days.

(21) Appl. No.: 14/700,531

(22) Filed: Apr. 30, 2015

(65) Prior Publication Data

US 2015/0320401 A1 Nov. 12, 2015

(30) Foreign Application Priority Data

May 8, 2014 (JP) .................................. 2014-097181

(51) Int. Cl.
*A61B 8/08* (2006.01)
*A61B 8/14* (2006.01)
(Continued)

(52) U.S. Cl.
CPC .......... *A61B 8/5276* (2013.01); *A61B 8/0841* (2013.01); *A61B 8/14* (2013.01);
(Continued)

(58) Field of Classification Search
CPC .......................... G01S 7/52033; A61B 8/5276
See application file for complete search history.

(56) References Cited

U.S. PATENT DOCUMENTS 4,043,181 A * 8/1977 Nigam ...................... A61B 8/08
  73/614
7,583,828 B2 * 9/2009 Hall ......................... A61B 8/08
  382/128
(Continued)

FOREIGN PATENT DOCUMENTS

DE 102013021729 A1 7/2014
JP 2001269339 A 10/2001

OTHER PUBLICATIONS

Shung, Diagnostic Ultrasound: Imaging and Blood Flow Measurement, 2006.*

(Continued)

*Primary Examiner* — Pascal M Bui Pho
*Assistant Examiner* — Colin T. Sakamoto
(74) *Attorney, Agent, or Firm* — Holtz, Holtz & Volek PC

(57) ABSTRACT

An ultrasound image processing method including: calculating motion amounts of pixel regions in one frame receive signal, based on receive signal units corresponding to identical pixel regions included in at least two frame receive signals; calculating cumulative motion amounts, each corresponding to a target pixel region in the one frame receive signal, by cumulating motion amounts corresponding to pixel regions in the one frame receive signal located substantially along a direction of transmission of the ultrasound beam from a pixel region located at an upstream end of an ultrasound beam to the target pixel region; calculating enhancement amounts for receive signal units corresponding to the pixel regions included in the one frame receive signal, the enhancement amounts being based on the motion amounts and the cumulative motion amounts; and enhancing the receive signal units based on the enhancement amounts.

11 Claims, 15 Drawing Sheets

Calculate cumulative motion amount of target pixel by cumulating motion amounts in each vertical direction (first direction)

Calculate maximum value of motion amount in horizontal direction (second direction)

(51) Int. Cl.
*A61B 8/00* (2006.01)
*G01S 7/52* (2006.01)
*G01S 15/89* (2006.01)

(52) U.S. Cl.
CPC .......... *A61B 8/5207* (2013.01); *A61B 8/5223* (2013.01); *A61B 8/5253* (2013.01); *A61B 8/54* (2013.01); *G01S 7/52063* (2013.01); *G01S 7/52077* (2013.01); *G01S 7/5208* (2013.01); *G01S 7/52046* (2013.01); *G01S 15/8915* (2013.01)

(56) References Cited

U.S. PATENT DOCUMENTS

2012/0253181 A1* 10/2012 Okamura ............. A61B 8/0841
  600/424
2014/0187942 A1  7/2014 Wang et al.

OTHER PUBLICATIONS

Extended European Search Report dated Oct. 7, 2015, issued in counterpart European Application No. 15166451.3.
Huang, et al., "Imaging Artifacts of Medical Instruments in Ultrasound-Guided Interventions", Journal of Ultrasound in Medicine, Oct. 1, 2007; p. 1303-1322; XP055215972; URL: http://www.jultrasoundmed.org/cgi/content/abstract/26/10/1303.

* cited by examiner

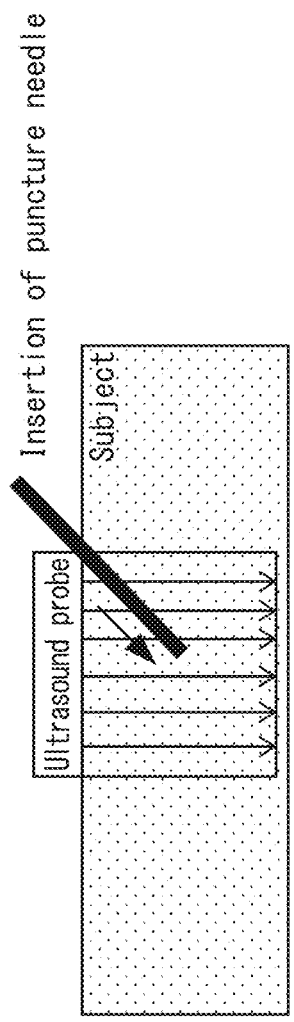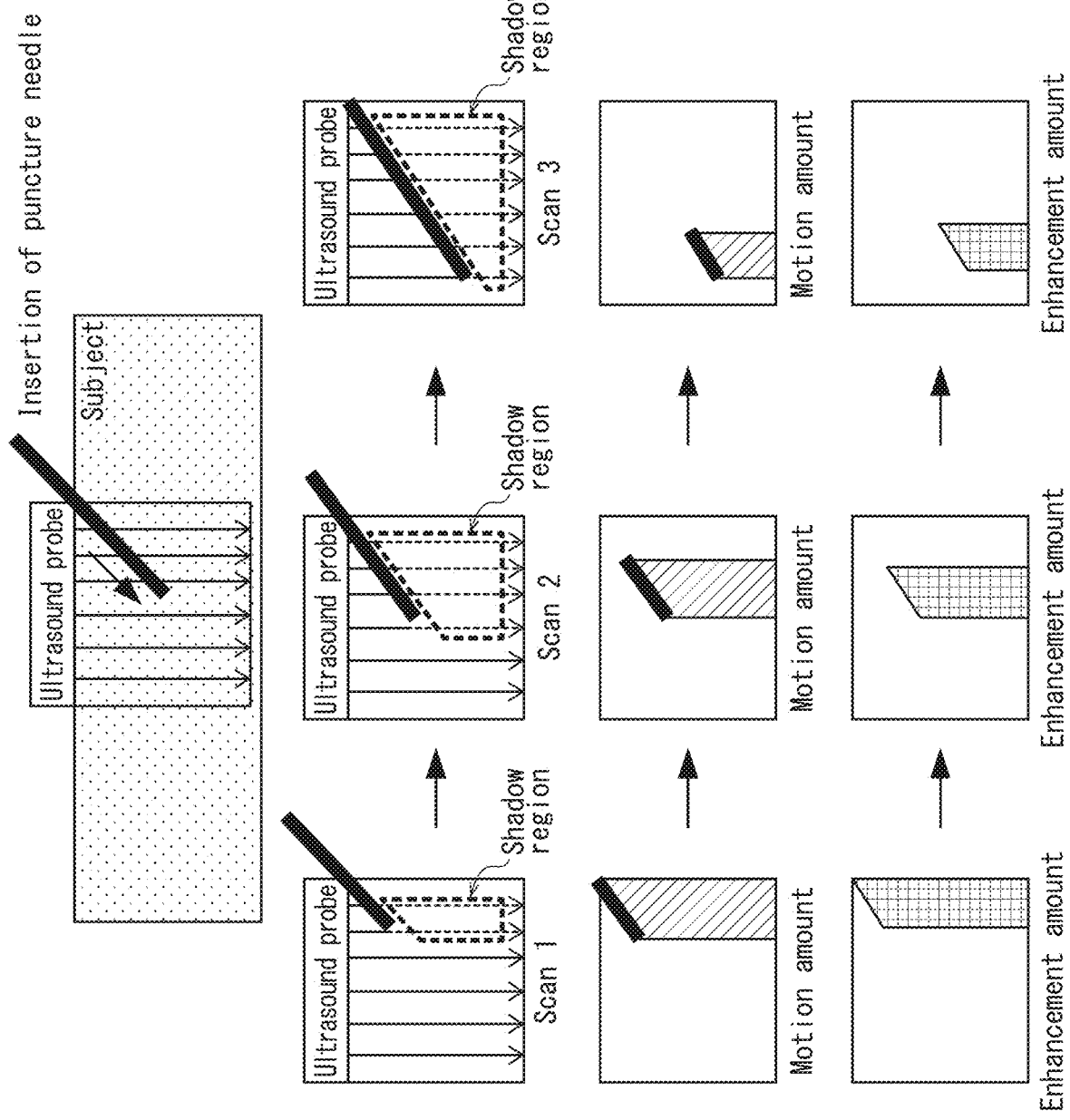
FIG. 17A  FIG. 17B  FIG. 17C  FIG. 17D

ULTRASOUND IMAGE PROCESSING METHOD AND ULTRASOUND DIAGNOSTIC DEVICE USING ULTRASOUND IMAGE PROCESSING METHOD

CROSS-REFERENCE TO RELATED APPLICATION

This application is based on an application No. 2014-097181 filed in Japan, the contents of which are hereby incorporated by reference.

BACKGROUND OF THE INVENTION (1) Field of the Invention

The present disclosure is related to ultrasound image processing methods and ultrasound diagnostic devices using such methods, in particular techniques for ultrasound imaging using puncture needles.

(2) Description of the Related Art

In recent years, tissues and fluids are being collected by insertion of puncture needles into bodies of patients, and biopsies are being performed examining said tissues and fluids. Further, in anesthesiology units, intensive care units, and pain clinics, anesthetic treatment using puncture needles is being performed. In diagnoses performed in such units, operators such as doctors view ultrasound images of a subject acquired by an ultrasound probe to confirm the position of a puncture needle and perform insertion of the puncture needle. At such time, it is necessary to confirm the position of the puncture needle, and particularly the tip thereof, on a monitor, and improvements are being sought in visibility of the puncture needle in ultrasound diagnostic devices.

Particularly in conditions in which an angle between an ultrasound beam and the puncture needle is small, such as when the puncture needle is inserted at an acute angle with respect to the subject, ultrasound reflected at the puncture needle and incoming to the ultrasound probe becomes weak and visualization of the puncture needle becomes insufficient. Thus, various studies have been made towards improving visibility of the puncture needle. For example, in an ultrasound diagnostic device, a method has been proposed of calculating a time difference of ultrasound tomographic image frame data and performing additional processing of spatial variation on the ultrasound tomographic image frame data (for example, Japanese Patent Application No. 2001-269339).

SUMMARY OF THE INVENTION

Problems to be Solved by the Invention

An ultrasound diagnostic device is a means of visualizing an ultrasound beam emitted from an ultrasound probe toward a subject and reflected back. Accordingly, when a substance having a significantly different refractive index from biological tissue, such as a puncture needle composed of metal, is irradiated by an ultrasound beam, cases occur in which the ultrasound beam is strongly reflected at the boundary between the puncture needle and the biological tissue and the ultrasound beam does not sufficiently reach areas deeper than the puncture needle, and such cases are associated with a problem of image quality deterioration.

The present disclosure is achieved in view of the above technical problem, and has an aim of providing an ultrasound image processing method and ultrasound diagnostic device using the ultrasound image processing method that increases visibility of a puncture needle in ultrasound image diagnosis while improving ease of use and preventing image quality deterioration due to influence of the puncture needle.

Means for Solving the Problems

In order to solve the above technical problem, an ultrasound image processing method pertaining to an aspect of the present disclosure is an ultrasound image processing method for correcting at least one of a plurality of frame receive signals generated based on ultrasound scans performed sequentially, an ultrasound probe transmitting an ultrasound beam towards a range to be scanned in a subject and receiving reflected ultrasound in each of the ultrasound scans, the ultrasound image processing method comprising: acquiring at least two of the frame receive signals; calculating motion amounts, each indicating motion of an object in the subject and corresponding to a respective one of a plurality of pixel regions in one of the two frame receive signals, each of the pixel regions indicating a region of at least one pixel, the calculating of each of the motion amounts being performed based on receive signal units corresponding to identical pixel regions included in the at least two of the frame receive signals; calculating cumulative motion amounts, each corresponding to a target pixel region in the one frame receive signal, by cumulating motion amounts corresponding to reference pixel regions in the one frame receive signal that are located substantially along a direction of transmission of the ultrasound beam from a pixel region located at an upstream end of the ultrasound beam to the target pixel region, each of the pixel regions included in the one frame receive signal being specified as the target pixel region; calculating enhancement amounts for receive signal units, each of the receive signal units corresponding to a respective one of the pixel regions included in the one frame receive signal, the enhancement amounts being based on the motion amounts and the cumulative motion amounts; and enhancing the receive signal units based on the enhancement amounts.

Further, an ultrasound diagnostic device pertaining to an aspect of the present disclosure is an ultrasound diagnostic device for correcting at least one of a plurality of frame receive signals generated based on ultrasound scans performed sequentially, an ultrasound probe transmitting an ultrasound beam towards a range to be scanned in a subject and receiving reflected ultrasound in each of the ultrasound scans, the ultrasound diagnostic device comprising: a control circuit, the control circuit comprising: a receive signal acquirer that acquires at least two of the frame receive signals; a motion calculator that calculates motion amounts, each indicating motion of an object in the subject and corresponding to a respective one of a plurality of pixel regions in one of the two frame receive signals, each of the pixel regions indicating a region of at least one pixel, the calculating of each of the motion amounts being performed based on receive signal units corresponding to identical pixel regions included in the at least two of the frame receive signals; a cumulative motion calculator that calculates cumulative motion amounts, each corresponding to a target pixel region in the one frame receive signal, by cumulating motion amounts corresponding to reference pixel regions in the one frame receive signal that are located substantially along a direction of transmission of the ultrasound beam from a pixel region located at an upstream end of the ultrasound beam to the target pixel region, each of the pixel regions included in the one frame receive signal being specified as the target pixel region; an enhancement calculator that calculates enhancement amounts for receive signal units, each of the receive signal units corresponding to a respective one of the pixel regions included in the one frame receive signal, the enhancement amounts being based on the motion amounts and the cumulative motion amounts; and a receive signal enhancer that enhances the receive signal units based on the enhancement amounts.

BRIEF DESCRIPTION OF THE DRAWINGS

These and the other objects, advantages and features of the invention will become apparent from the following description thereof taken in conjunction with the accompanying drawings which illustrate a specific embodiment of the invention.

In the drawings:

FIGS. 17A-17D are schematic diagrams for describing pseudo-enhancement of a puncture needle shadow portion associated with puncture needle enhancement processing in the conventional ultrasound diagnostic device 10X.

DESCRIPTION OF THE PREFERRED EMBODIMENT

The following describes the preferred embodiment.

<Developments that LED to the Embodiments of the Present Invention>

Figure 13:
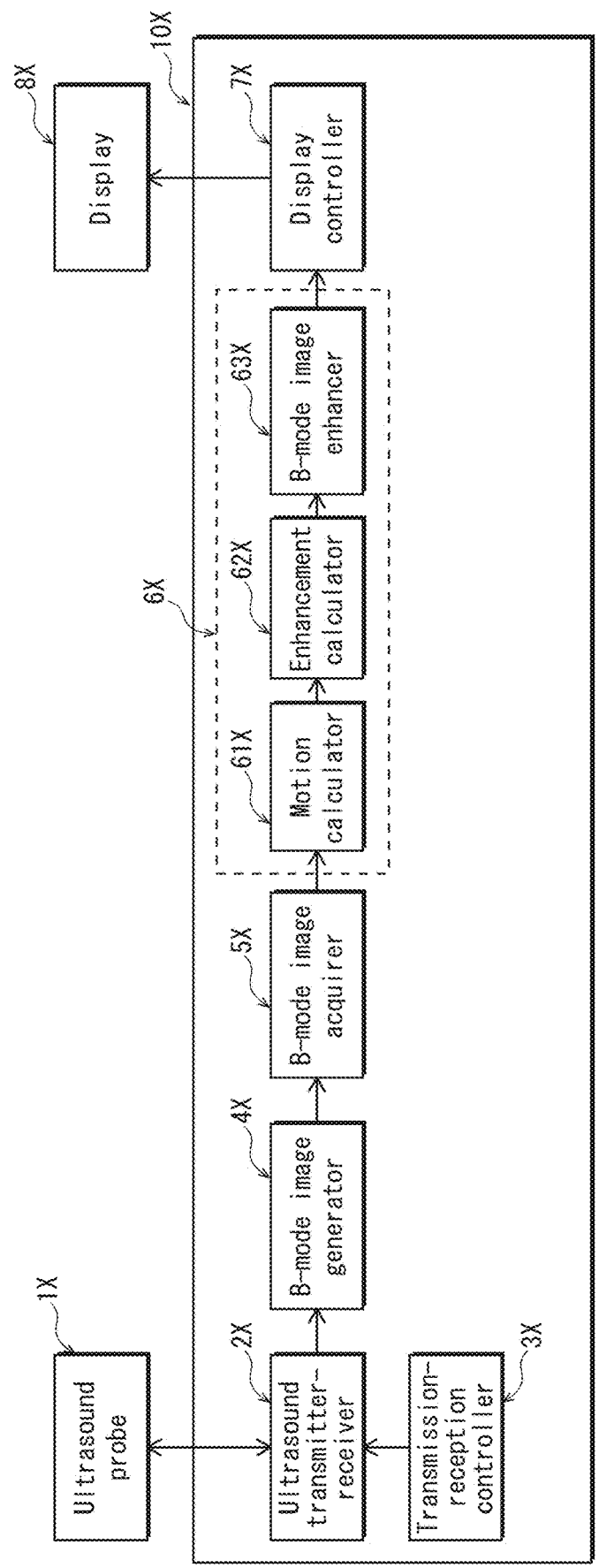
FIG. 13 is a function block diagram of a conventional ultrasound diagnostic device 10X.

The inventors performed various studies into improving visibility of a puncture needle in ultrasound image diagnosis. FIG. 13 is a block diagram indicating a configuration of a conventional ultrasound diagnostic device 10X. The ultrasound diagnostic device 10X includes an ultrasound transmitter-receiver 2X, a transmission-reception controller 3X, a B-mode image generator 4X, a B-mode image acquirer 5X, an enhancement processor 6X, and a display controller 7X. The enhancement processor includes a motion calculator 61X, an enhancement calculator 62X, and a B-mode image enhancer 63X. Further, an ultrasound probe 1X and a display 8X are configured to be connectable to the ultrasound transmitter-receiver 2X and the display controller 7X, respectively.

The following describes operation of the ultrasound diagnostic device 10X. The ultrasound transmitter-receiver 2X, based on a transmission control signal from the transmission-reception controller 3X, performs transmission processing supplying a pulsed transmit ultrasound signal to the ultrasound probe 1X, causing the ultrasound probe 1X to transmit an ultrasound beam towards a scanning area of a subject. The ultrasound transmitter-receiver 2X further generates acoustic line signals that are continuous in a depth direction by delay-and-sum processing of radio frequency (RF) signals after amplification and audio-digital (AD) conversion of ultrasound signals based on reflected ultrasound acquired from the ultrasound probe 1X, and outputs a sequence of ultrasound scans to the B-mode image acquirer 5X. When the ultrasound scanning is performed, the ultrasound transmitter-receiver sequentially outputs the acoustic line signals to the B-mode image generator 4X.

The B-mode image generator 4X executes processing such as envelope detection and logarithmic compression on the acoustic line signals to convert them into luminance, and generates a B-mode image signal by performing coordinate transformation to an orthogonal coordinate system on the luminance. Each B-mode image signal generated at the B-mode image generator 4X is transmitted to the B-mode image acquirer 5X each time the ultrasound scanning is performed, and is stored by the B-mode image acquirer. The B-mode image acquirer 5X is a buffer that stores B-mode image signals.

Figure 14:
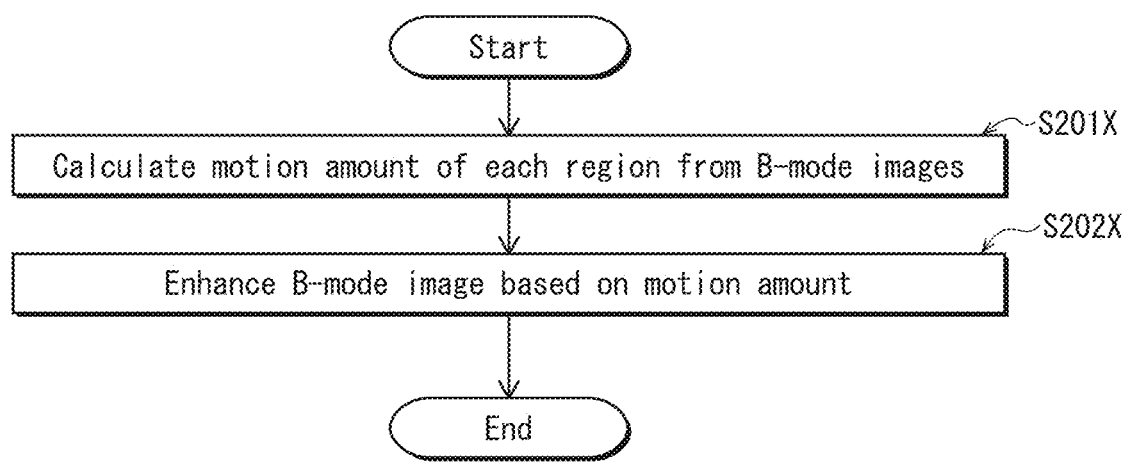
FIG. 14 is a flowchart indicating operation of an enhancement processor 6X in the conventional ultrasound diagnostic device 10X.

Next, in the enhancement processor 6X, enhancement processing is performed on the B-mode image signals. FIG. 14 is a flowchart indicating operation of the enhancement processor 6X in the ultrasound diagnostic device 10X;

In step S201X, the motion calculator 61X reads two frames from the B-mode image acquirer 5X, a current frame and a frame prior to the current fame, and calculates an inter-frame difference for each pixel thereof. The inter-frame difference is a difference between luminance indicated in the B-mode image signal of the current frame and luminance indicated in the B-mode image signal of a prior frame acquired from the same location in the subject as the current frame. The inter-frame difference is substantially proportional to a motion amount indicating motion of an object. By using the above inter-frame difference, etc., a portion of the B-mode image signal indicating motion of a puncture needle can be extracted.

In step S202X, the enhancement calculator 62X calculates enhancement amounts based on the motion amounts, the B-mode image enhancer 63X enhances the B-mode image signal pixel-by-pixel, based on the enhancement amounts, the enhanced B-mode image signal is outputted to the display controller 7X, and the enhanced B-mode image is displayed on the display 8X. Enhancement amounts can be determined per pixel by a condition according to which the enhancement amount of the B-mode image signal is proportional to the motion amount indicated by the inter-frame difference.

Figure 15:
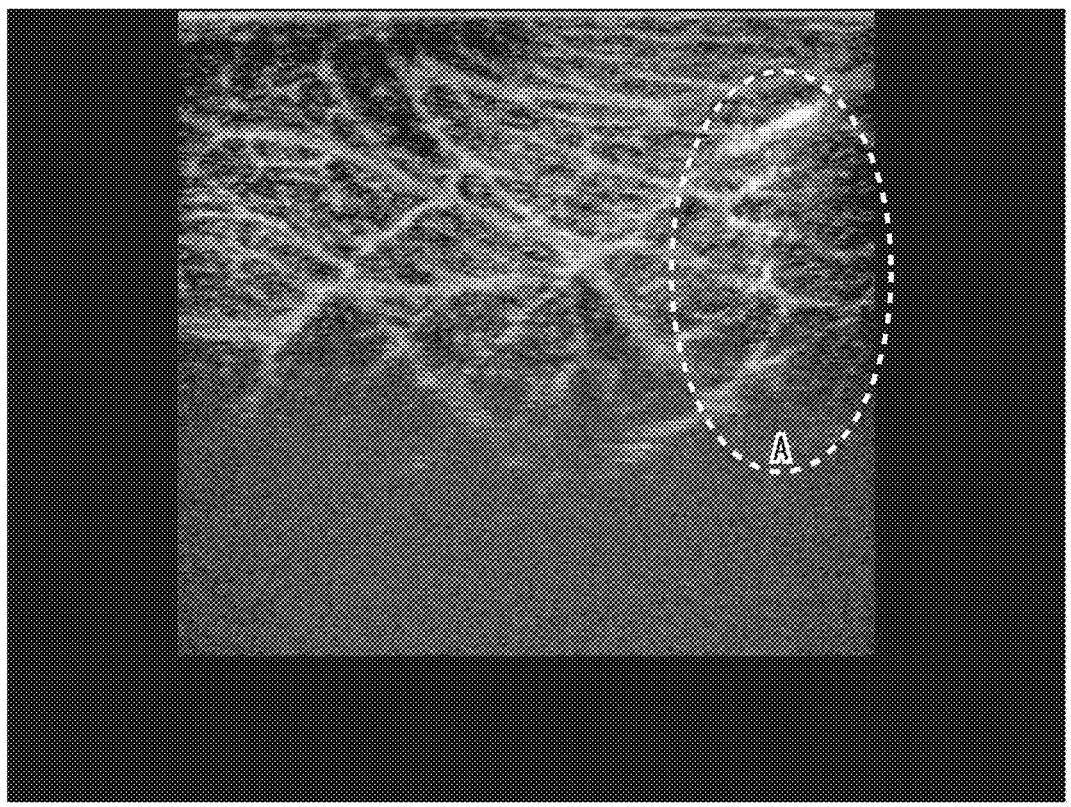
FIG. 15 is a B-mode image acquired by the conventional ultrasound diagnostic device 10X.
Figure 16:
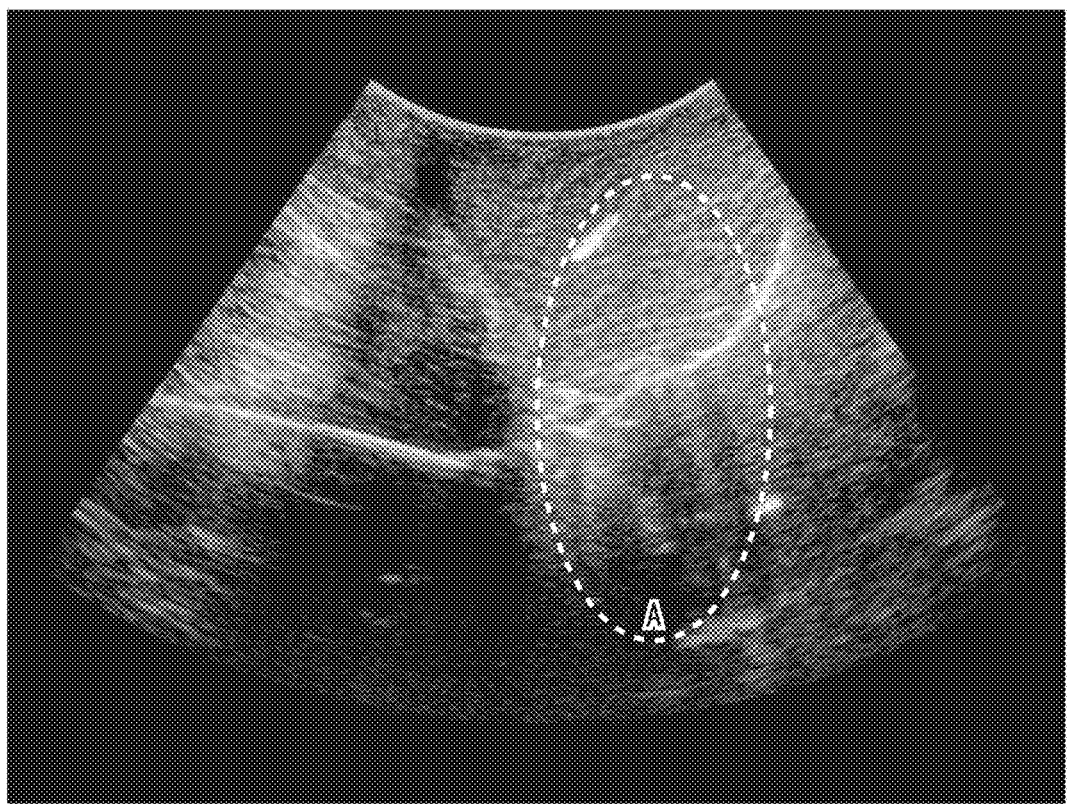
FIG. 16 is a B-mode image acquired by the conventional ultrasound diagnostic device 10X.

FIG. 15 and FIG. 16 are B-mode images acquired by the conventional ultrasound diagnostic device 10X. In FIG. 15 and FIG. 16, in each region A surrounded by a dashed line, the white speckled portion in an upper portion of the region A is a display image of a puncture needle that has been enhanced. Further, below the display image of the puncture needle in the region A is a white-colored part. This is a shadow of the puncture needle having been pseudo-enhanced, and may be considered noise associated with the puncture needle enhancement processing. The following describes reasons for occurrence of pseudo-enhancement of the shadow of the puncture needle, with reference to the drawings.

FIGS. 17A-17D are schematic diagrams for describing pseudo-enhancement of a puncture needle shadow portion associated with puncture needle enhancement processing in the conventional ultrasound diagnostic device 10X. In ultrasound diagnosis using a puncture needle, the puncture needle is inserted into a scanning region to which an ultrasound beam is transmitted from an ultrasound probe towards a subject (FIG. 17A). At this time, along with insertion of the puncture needle, a shadow region that is insufficiently irradiated by the ultrasound beam occurs below the puncture needle (FIG. 17B). As described above, an enhancement amount of each pixel is calculated according to a motion amount indicated by an inter-frame difference of each pixel in, for example, a current frame and an immediately prior frame of a B-mode image signal. Thus, in FIG. 17B, the portion that is newly shadowed by insertion of the puncture needle is regarded as having changed in luminance compared to the immediately prior frame, and therefore a motion amount is detected according to the amount of change in luminance (FIG. 17C). As a result, an enhancement amount corresponding to the luminance change is assigned to pixels in the portion newly shadowed along with insertion of the puncture needle, and said pixels are enhanced in the B-mode image signal (FIG. 17D).

Such pseudo-enhancement of the puncture needle shadow is an artifact that does not exist in the originally measured object, and is undesirable when performing an efficient and appropriate diagnosis. Thus, the inventors performed intensive investigations into techniques preventing occurrence of pseudo-enhancement when performing enhancement processing of a puncture needle in puncture needle enhancement processing of a B-mode image, and arrived at the idea of the ultrasound image processing method and the ultrasound diagnostic device using the ultrasound image processing method pertaining to the embodiments of the present invention.

The following describes details of the ultrasound image processing method and the ultrasound diagnostic device using the ultrasound image processing method pertaining to the embodiments of the present invention, with reference to the drawings.

Summary of Embodiments of the Present Invention

An ultrasound image processing method pertaining to the present embodiment is an ultrasound image processing method for correcting at least one of a plurality of frame receive signals generated based on ultrasound scans performed sequentially, an ultrasound probe transmitting an ultrasound beam towards a range to be scanned in a subject and receiving reflected ultrasound in each of the ultrasound scans, the ultrasound image processing method comprising: acquiring at least two of the frame receive signals; calculating motion amounts, each indicating motion of an object in the subject and corresponding to a respective one of a plurality of pixel regions in one of the two frame receive signals, each of the pixel regions indicating a region of at least one pixel, the calculating of each of the motion amounts being performed based on receive signal units corresponding to identical pixel regions included in the at least two of the frame receive signals; calculating cumulative motion amounts, each corresponding to a target pixel region in the one frame receive signal, by cumulating motion amounts corresponding to reference pixel regions in the one frame receive signal that are located substantially along a direction of transmission of the ultrasound beam from a pixel region located at an upstream end of the ultrasound beam to the target pixel region, each of the pixel regions included in the one frame receive signal being specified as the target pixel region; calculating enhancement amounts for receive signal units, each of the receive signal units corresponding to a respective one of the pixel regions included in the one frame receive signal, the enhancement amounts being based on the motion amounts and the cumulative motion amounts; and enhancing the receive signal units based on the enhancement amounts.

Further, according to another aspect, when the direction is a first direction, the reference pixel regions may be located along a straight line parallel to the first direction from a pixel region located at the upstream end of the ultrasound beam to the target pixel region.

Further, according to another aspect, a second direction is perpendicular to the direction, and each of the reference pixel regions may be a pixel region corresponding to a greatest motion amount among motion amounts corresponding to pixel regions in a linear sequence in the second direction.

Further, according to another aspect, the enhancement amounts may be increased in proportion to the motion amounts, and when a given one of the cumulative motion amounts exceeds a predefined reference value, a corresponding one of the enhancement amounts may be decreased in proportion to an amount by which the predefined reference value is exceeded.

Further, according to another aspect, the reference pixel regions may be located along the transmit direction of the ultrasound beam.

Further, according to another aspect, the motion amounts may be determined based on differences between luminance indicated by the receive signal units in the one frame receive signal and luminance indicated by receive signal units corresponding to identical pixel regions in a frame receive signal generated based on an ultrasound scan prior to an ultrasound scan corresponding to the one frame receive signal, and the motion amount may be proportional to size of the difference.

Further, according to another aspect, luminance indicated by the receive signal units may be increased in proportion to the enhancement amounts.

Further, according to another aspect, color indicated by the receive signal units may be changed based on the enhancement amounts.

Further, according to another aspect, enhancement effect duration with respect to the receive signal units may be increased in proportion to the enhancement amounts.

Further, according to another aspect, a puncture needle is inserted within the scanning range in the subject, and the enhancement amounts may be large for receive signal units of the one frame receive signal in which the puncture needle is indicated.

Further, according to another aspect, the one frame receive signal may be one of a frame B-mode image signal and a frame acoustic line signal.

Further, according to another aspect, a computer-readable non-transitory storage medium may store a program executable by a computer to perform the above ultrasound image processing method.

Further, an ultrasound diagnostic device pertaining to the present embodiment is an ultrasound diagnostic device for correcting at least one of a plurality of frame receive signals generated based on ultrasound scans performed sequentially, an ultrasound probe transmitting an ultrasound beam towards a range to be scanned in a subject and receiving reflected ultrasound in each of the ultrasound scans, the ultrasound diagnostic device comprising: a control circuit, the control circuit comprising: a receive signal acquirer that acquires at least two of the frame receive signals; a motion calculator that calculates motion amounts, each indicating motion of an object in the subject and corresponding to a respective one of a plurality of pixel regions in one of the two frame receive signals, each of the pixel regions indicating a region of at least one pixel, the calculating of each of the motion amounts being performed based on receive signal units corresponding to identical pixel regions included in the at least two of the frame receive signals; a cumulative motion calculator that calculates cumulative motion amounts, each corresponding to a target pixel region in the one frame receive signal, by cumulating motion amounts corresponding to reference pixel regions in the one frame receive signal that are located substantially along a direction of transmission of the ultrasound beam from a pixel region located at an upstream end of the ultrasound beam to the target pixel region, each of the pixel regions included in the one frame receive signal being specified as the target pixel region; an enhancement calculator that calculates enhancement amounts for receive signal units, each of the receive signal units corresponding to a respective one of the pixel regions included in the one frame receive signal, the enhancement amounts being based on the motion amounts and the cumulative motion amounts; and a receive signal enhancer that enhances the receive signal units based on the enhancement amounts.

Further, according to another aspect, when the direction is a first direction, the reference pixel regions are located along a straight line parallel to the first direction from a pixel region located at the upstream end of the ultrasound beam to the target pixel region.

Further, according to another aspect, a second direction is perpendicular to the direction, and each of the reference pixel regions may be a pixel region corresponding to a greatest motion amount among motion amounts corresponding to pixel regions in a linear sequence in the second direction.

Further, according to another aspect, the receive signal enhancer increases the enhancement amounts in proportion to the motion amounts, and when a given one of the cumulative motion amounts exceeds a predefined reference value, decreases a corresponding one of the enhancement amounts in proportion to an amount by which the predefined reference value is exceeded.

Embodiment 1

The following describes the ultrasound diagnostic device pertaining to embodiment 1, with reference to the drawings.

<Overall Structure>

1. Ultrasound Diagnostic Device 10

Figure 1:
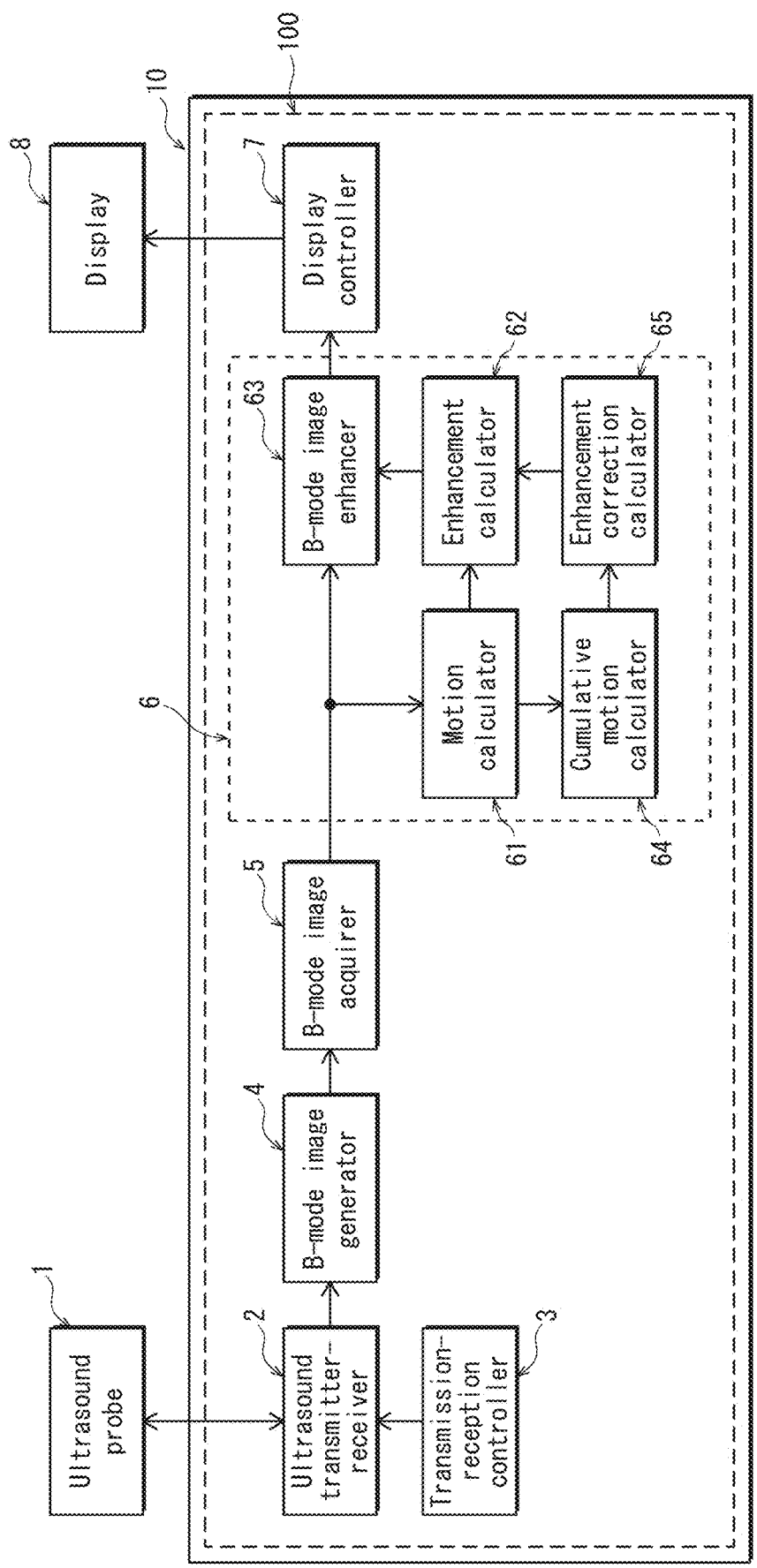
FIG. 1 is a function block diagram of an ultrasound diagnostic device 10 pertaining to embodiment 1.

FIG. 1 is a function block diagram of the ultrasound diagnostic device 10 pertaining to embodiment 1. The ultrasound diagnostic device 10 includes a control circuit 100 provided with an ultrasound transmitter-receiver 2, a transmission-reception controller 3, a B-mode image generator 4, a B-mode image acquirer 5, an enhancement processor 6, and a display controller 7.

Each element of the control circuit 100 is implemented by a hardware circuit such as a field programmable gate array (FPGA), application specific integrated circuit (ASIC), etc. Alternatively, each element may be implemented by software and a programmable device such as a central processing unit (CPU), general-purpose computing on a graphics processing unit (GPGPU), a processor, etc. Such elements may be implemented as separate circuit components, or as an assembly of a plurality of circuit components. Further, a plurality of elements may be assembled as one circuit component and a plurality of circuit components may be integrated. Further, an ultrasound probe 1 and a display 8 are configured to be connectable to the ultrasound transmitter-receiver 2 and the display controller 7, respectively. FIG. 1 shows the ultrasound diagnostic device 10 connected to the ultrasound probe 1 and the display 8.

The following describes each element connected externally to the ultrasound diagnostic device 10.

2. Ultrasound Probe

The ultrasound probe 1 has a plurality of transducers (not illustrated) arranged, for example, in a one-dimensional direction (hereafter, "transducer array direction"). The ultrasound probe 1 converts pulsed electrical signals (hereafter, "transmit ultrasound signals") supplied from the ultrasound transmitter-receiver 2 (described later) into pulsed ultrasound. The ultrasound probe 1, in a state in which a transducer-side outer surface of the ultrasound probe 1 is in contact with a skin surface of a subject, transmits an ultrasound beam composed of a plurality of ultrasound waves emitted from the plurality of transducers towards a measurement object. Subsequently, the ultrasound probe 1 receives a plurality of reflected ultrasound waves from the subject, the plurality of transducers convert the plurality of reflected ultrasound waves into electrical signals (hereafter, "received ultrasound wave signals"), and the ultrasound probe 1 supplies the received ultrasound wave signals to the ultrasound transmitter-receiver 2.

In embodiment 1, the ultrasound probe 1 that has a plurality of transducers arranged in a one-dimensional direction is indicated as an example, but the ultrasound probe 1 that can be used in the present embodiment is not limited in this way. For example, a two-dimensional array of transducers arranged in two-dimensional directions, or a plurality of transducers arranged in a one-dimensional direction and mechanically caused to swing in an oscillating ultrasound probe obtaining three-dimensional tomographic images may be used, and can be appropriately selected according to measurements to be acquired.

Further, the ultrasound probe 1 may be provided with a portion of the functions of the ultrasound transmitter-receiver 2. For example, a function of generating a transmit electrical signal in the ultrasound probe 1 based on a control signal (hereafter, "transmit control signal") for generating the transmit electrical signal outputted from the ultrasound transmitter-receiver 2 and converting the transmit electrical signal into ultrasound may be provided on the ultrasound probe side. Further, a function of, after received reflected ultrasound is converted into receive electrical signals, generating a receive signal (described later) based on the receive electrical signals may be provided on the ultrasound probe side.

3. Display 8

The display 8 is a display device for image display that displays image output from the display controller 7 (described later) on a display screen. A liquid crystal display, CRT, organic EL display, etc., can be used as the display 8.

<Component Configuration>

The following describes configurations of each block included in the ultrasound diagnostic device 10.

1. Ultrasound Transmitter-Receiver 2

The ultrasound transmitter-receiver 2 is connected to the ultrasound probe 1. The ultrasound transmitter-receiver 2 is a circuit that, based on a transmission control signal from the transmission-reception controller 3, performs transmission processing supplying a pulsed transmit ultrasound signal to the ultrasound probe 1, causing the ultrasound probe 1 to transmit an ultrasound beam. Specifically, the ultrasound transmitter-receiver 2 includes, for example, a clock generating circuit, a pulse generating circuit, and a delay circuit. The clock generating circuit is a circuit generating a clock signal determining transmit timing of an ultrasound beam. The pulse generating circuit is a circuit for generating pulse signals driving the transducers. The delay circuit is a circuit for performing focusing and steering of an ultrasound beam by delaying transmission of the ultrasound beam by a delay time that sets a transmit timing of the ultrasound beam for each transducer.

The ultrasound transmitter-receiver 2 further generates an acoustic line signal that is continuous in a depth direction by delay-and-sum processing of RF signals after amplification and AD conversion of received ultrasound wave signals based on reflected ultrasound acquired from the ultrasound probe 1. Subsequently, the ultrasound transmitter-receiver 2 sequentially outputs acoustic line signals to the B-mode image generator 4 in the order of sub-scanning.

RF signals are, for example, composed of a plurality of signals from a direction perpendicular to the transducer array (the transmit direction of ultrasound and the transducer array direction, respectively), each signal being a digital signal after AD conversion of an electrical signal converted from an amplitude of reflected ultrasound.

The acoustic line signals are continuous data in a depth direction that include RF signals after delay-and-sum processing. The depth direction is a direction of travel of a transmitted ultrasound signal, from a body surface of a subject into the body. The acoustic line signals, for example, construct a frame composed of a plurality of signals from the direction perpendicular to the transducer array (the transmit direction of ultrasound and the transducer array direction, respectively). Acoustic line signals acquired by one ultrasound scan are referred to as a frame acoustic line signal. Here, "frame" indicates a unit of one unified signal required to construct a single tomographic image.

The ultrasound transmitter-receiver 2 continuously repeats transmit processing and receive processing.

2. Transmission-Reception Controller 3

The transmission-reception controller 3 is a circuit that generates and outputs transmit control signals and receive control signals to the ultrasound transmitter-receiver 2. In the present embodiment, in the transmit control signals and the receive control signals, information indicating transmission and reception timing, etc., is outputted to the ultrasound transmitter-receiver 2.

3. B-Mode Image Generator 4

The B-mode image generator 4 is a circuit that converts each acoustic line signal in a frame into a luminance signal corresponding to intensity of the acoustic line signal, and generates a frame B-mode image signal by performing coordinate transformation on the luminance signals to an orthogonal coordinate system. The B-mode image generator 4 processes each frame in sequence and outputs generated tomographic images to the B-mode image acquirer 5. Specifically, the B-mode image generator 4 executes processing such as envelope detection and logarithmic compression on the acoustic line signals to convert them into luminance, and generates a B-mode image signal by performing coordinate transformation on the luminance to an orthogonal coordinate system. In other words, the B-mode image signal expresses intensity of ultrasound receive signals as luminance. The frame B-mode image signals generated by the B-mode image generator 4 are sequentially transmitted to the B-mode image acquirer 5 as each ultrasound scan is performed.

4. B-Mode Image Acquirer 5

The B-mode image acquirer 5 is a circuit provided with a buffer that stores frame B-mode image signals sequentially transmitted as each ultrasound scan is performed, as input of B-mode image signals generated by the B-mode image generator.

In the present specification, a B-mode image signal or an acoustic line signal that is a base for generating a B-mode image signal is also referred to as a receive signal or an ultrasound receive signal.

5. Enhancement Processor 6

The enhancement processor 6 includes a motion calculator 61, an enhancement calculator 62, a cumulative motion calculator 64, an enhancement correction calculator 65, and a B-mode image enhancer 63.

(5.1) Motion Calculator 61

The motion calculator 61 is a circuit that calculates motion amounts, each indicating motion of an object in frame B-mode image signals by calculating an inter-frame difference of luminance indicated by the frame B-mode image signals acquired from the B-mode image acquirer 5. Here, "object in a pixel region" indicates tissue of a subject or an artificial object such as a puncture needle inserted into tissue of the subject, the tissue or artificial object being indicated by an image of a pixel region. In the present embodiment, the motion calculator 61 calculates motion amounts indicating motion of a puncture needle. Specifically, the motion calculator 61 reads, from the B-mode image acquirer 5, at least two frame B-mode image signals including the current frame, and performs a calculation of an inter-frame difference of luminance, for example, between identical pixel regions in the at least two frame B-mode image signals, the pixel regions indicating a region of at least one pixel. Subsequently, the motion calculator 61 calculates motion amounts according to a condition that the motion amounts corresponding to the pixel regions of the current frame B-mode image signal increase in proportion to increases in the values of the inter-frame differences of the identical pixel regions. The motion amounts calculated for each pixel region included in the frame B-mode image signal are outputted to the enhancement calculator 62 and the cumulative motion calculator 64.

(5.2) Cumulative Motion Calculator 64

The cumulative motion calculator 64 is a circuit that calculates cumulative motion amounts, each corresponding to a target pixel region in the frame B-mode image signal, by cumulating motion amounts corresponding to pixel regions in the frame B-mode image signal that are located substantially along a direction substantially parallel to the ultrasound beam transmission direction from a pixel region located at an upstream end of the ultrasound beam to the target pixel region, each of the pixel regions included in the frame B-mode image signal being specified as the target pixel region.

Here, "a direction substantially parallel to the ultrasound beam transmission direction" (hereafter, "first direction") indicates a direction with an angle no greater than 45 degrees between the direction and the ultrasound beam transmission direction in a frame B-mode image display. Further the "ultrasound beam transmission direction" indicates a depth direction of the acoustic line signal in a B-mode image display. For example, when a B-mode image is displayed, in orthogonal coordinates, from an x direction and y direction arbitrarily set on the B-mode image, a direction having the smallest angle between the direction and the depth direction of the acoustic line signal in the B-mode image is the first direction.

In the present embodiment, the cumulative motion calculator 64 calculates cumulative motion amounts, each corresponding to a target pixel region, by cumulating motion amounts corresponding to pixel regions that are located along a straight line parallel to the first direction that passes through the target pixel region from a pixel region located at an upstream end of the ultrasound beam to the target pixel region, each of the pixel regions included in the current frame B-mode image signal being specified as the target pixel region. Each of the cumulative motion amounts calculated for the pixel regions included in the frame B-mode image signal is outputted to the enhancement correction calculator 65.

(5.3) Enhancement Correction Calculator 65

The enhancement correction calculator 65 is a circuit that calculates an enhancement amount correction for each pixel region, based on the cumulative motion amount of each pixel region of a frame B-mode image signal. The enhancement amount correction for each pixel region is calculated to reduce an enhancement amount for the pixel region proportional to an amount of excess by which a corresponding cumulative motion amount exceeds a predefined reference value. The enhancement correction calculator 65 outputs the enhancement amount correction calculated for each pixel region to the enhancement calculator 62.

(5.4) Enhancement Calculator 62

The enhancement calculator 62 is a circuit that acquires motion amounts corresponding to the pixel regions from the motion calculator 61 and the enhancement amount correction for each of the pixel regions from the enhancement correction calculator 65; and calculates an enhancement amount for each pixel based on the motion amounts of the pixel regions of the frame B-mode image signal. The enhancement amount for each pixel region is calculated by increasing the enhancement amount with respect to the B-mode image signal of the pixel region by an amount proportional to the motion amount of the pixel region, and decreasing the enhancement amount based on the enhancement amount correction for the pixel region.

(5.5) B-Mode Image Enhancer 63

The B-mode image enhancer 63 is a circuit that acquires the frame B-mode image signal from the B-mode image acquirer 5 and the enhancement amount for each pixel region of the frame B-mode image signal from the enhancement calculator 62; and performs enhancement processing with respect to a B-mode image signal unit corresponding to respective ones of the pixel regions of the frame B-mode image signal. At this time, the B-mode image enhancer 63 performs enhancement processing for the B-mode image signal unit to increase luminance indicated by a receive signal unit of a target pixel region by an amount proportional to the enhancement amount. The B-mode image enhancer 63 outputs the frame B-mode image signal that has been enhanced to the display controller 7.

6. Display Controller 7

The display controller 7 is a circuit that causes the externally connected display 8 to display a B-mode image based on the frame B-mode image signal that has been enhanced.

<Operation>

Figure 2:
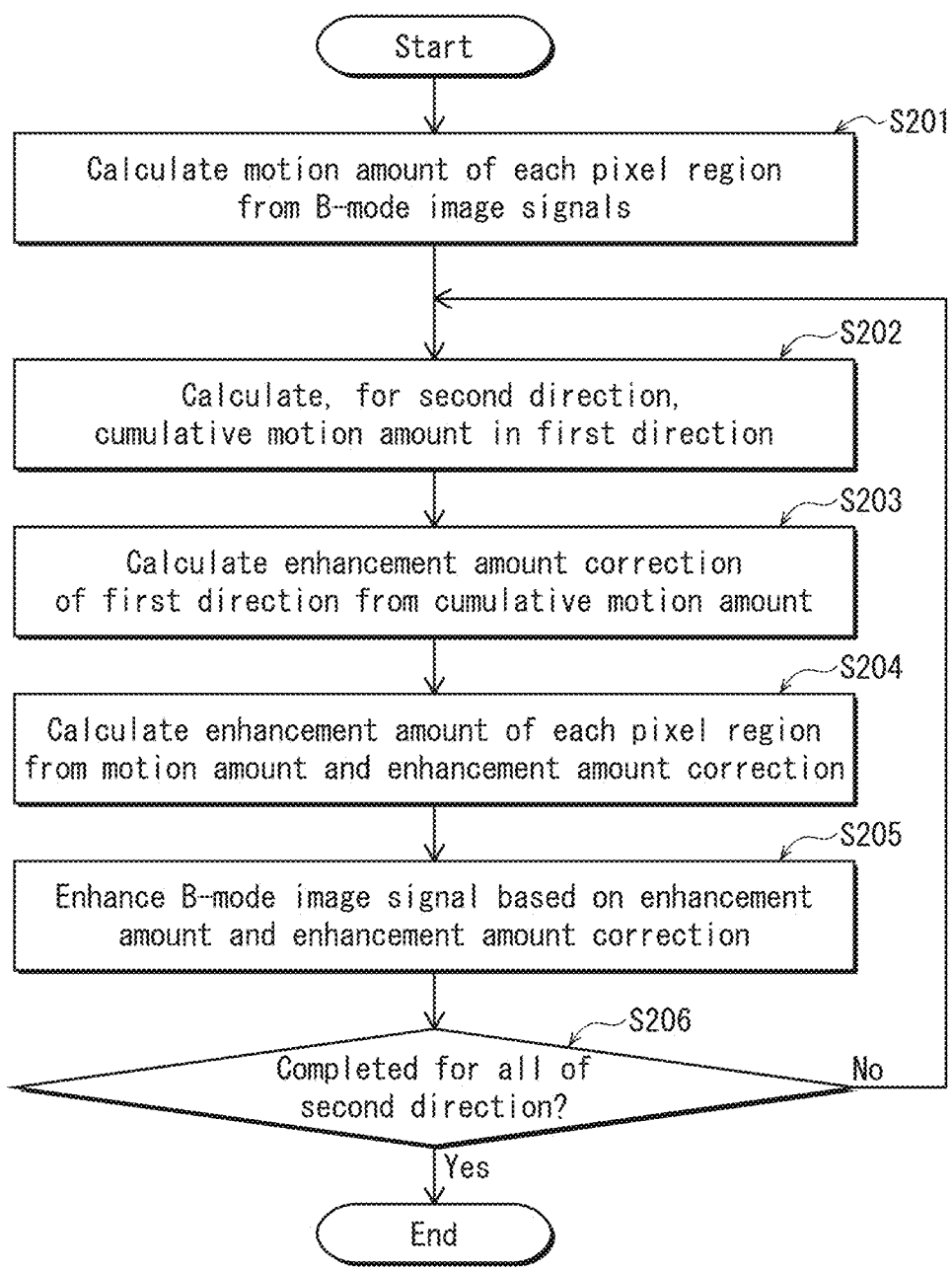
FIG. 2 is a flowchart indicating operation of an enhancement processor 6 in the ultrasound diagnostic device 10 pertaining to embodiment 1.

The following describes operation of the ultrasound diagnostic device 10 configured as described above. FIG. 2 is a flowchart indicating operation of the enhancement processor 6 in the ultrasound diagnostic device 10 pertaining to embodiment 1.

1. Step S201

In step S201, a motion amount of each pixel region from a plurality of frame B-mode image signals is calculated. According to an inter-frame difference of each pixel region of the frame B-mode image signals a motion amount of an object in the frame B-mode image signals is calculated. Specifically, the motion calculator 61 reads, from the B-mode image acquirer 5, at least two frame B-mode image signals including the current frame, and performs a calculation of an inter-frame difference of luminance, for example, between identical pixel regions composed of at least one pixel in the at least two frame B-mode image signals. The inter-frame difference is a difference between luminance indicated in the current frame B-mode image signal and luminance indicated in at least one frame B-mode image signal acquired before the current frame B-mode image signal in identical pixel regions composed of at least one pixel. In a case in which each of the pixel regions is composed of a plurality of pixels, a difference in luminance between the pixel regions can be calculated using an average luminance of each of the plurality of pixels. Further, in a case in which the inter-frame difference uses at least three frame B-mode image signals, a configuration may be used that calculates an average and variance of a plurality of inter-frame difference results between two frames, for example. Subsequently, the motion calculator 61 calculates motion amounts so that the motion amounts in the pixel regions of the current frame B-mode image signal increase in proportion to increases in the calculated values corresponding to identical pixel regions.

2. Step S202

In step S202, the cumulative motion calculator 64 calculates a cumulative motion amount of a target pixel region by cumulating motion amounts of each pixel region along a straight line parallel to the first direction, which is substantially parallel to the ultrasound beam transmission direction, and passes through the target pixel region, from a pixel region at an upstream end of the ultrasound beam to the location of the target pixel region; and calculates a cumulative motion amount of each pixel region by performing this cumulating for each location in a second direction perpendicular to the first direction and for each pixel region included in the current frame B-mode image signal.

3. Step S203

In step S203, the enhancement correction calculator 65 calculates an enhancement amount correction for each pixel region, based on the cumulative motion amount of each pixel region of the frame B-mode image signal. The enhancement amount correction for each pixel region is calculated to reduce an enhancement amount for the pixel region proportional to an amount of excess by which a corresponding cumulative motion amount exceeds a predefined reference value.

4. Step S204

In step S204, the enhancement calculator 62 calculates an enhancement amount for each pixel of the frame B-mode image signal, based on the motion amount of each pixel region supplied from the motion calculator 61 and the enhancement amount correction for each pixel region supplied from the enhancement correction calculator 65. The enhancement amount for each pixel region is calculated by increasing an enhancement amount with respect to the B-mode image signal of the pixel region by an amount proportional to the motion amount of the pixel region, and decreasing the enhancement amount based on the enhancement amount correction for the pixel region.

5. Step S205

The B-mode image enhancer 63 performs enhancement processing with respect to the B-mode image signal unit of each pixel region of the frame B-mode image signal, based on the frame B-mode image signal supplied from the B-mode image acquirer 5 and the enhancement amount for each pixel region of the frame B-mode image signal supplied from the enhancement calculator 62. At this time, the B-mode image enhancer 63 performs enhancement processing for the B-mode image signal to increase luminance indicated by a B-mode signal unit of a target pixel region by an amount proportional to the enhancement amount. This processing is performed at each location in the second direction perpendicular to the first direction (S206), and generates an enhanced frame B-mode image signal that has been enhanced.

The enhanced frame B-mode image signal is outputted to the image controller 7, the enhanced frame B-mode image signal is displayed on the display 8, and processing to update and display the enhanced frame B-mode image is performed each time the ultrasound scan is performed.

Preventing Pseudo-Enhancement in Puncture Needle Enhancement Processing

The following describes the effect of preventing pseudo-enhancement in puncture needle enhancement processing in the ultrasound diagnostic device 10, with reference to the drawings.

Figure 3:
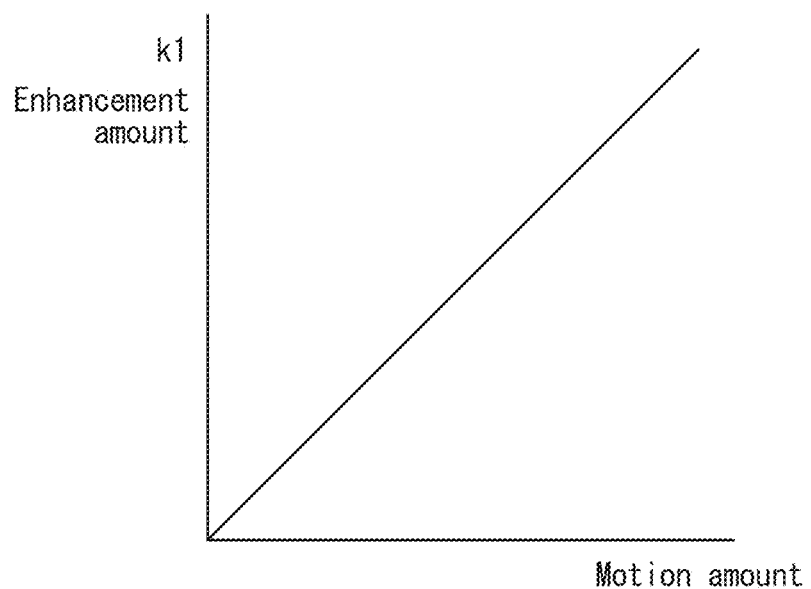
FIG. 3 is a graph indicating a relationship between input and output in an enhancement calculator 62 of the ultrasound diagnostic device 10 pertaining to embodiment 1.

FIG. 3 is a graph indicating a relationship between the motion amount, which is input, and a calculated enhancement amount k1 in the enhancement calculator 62 of the ultrasound diagnostic device 10. In the present embodiment, as shown in FIG. 3, the enhancement amount k1 is proportional to the motion amount.

Figure 4:
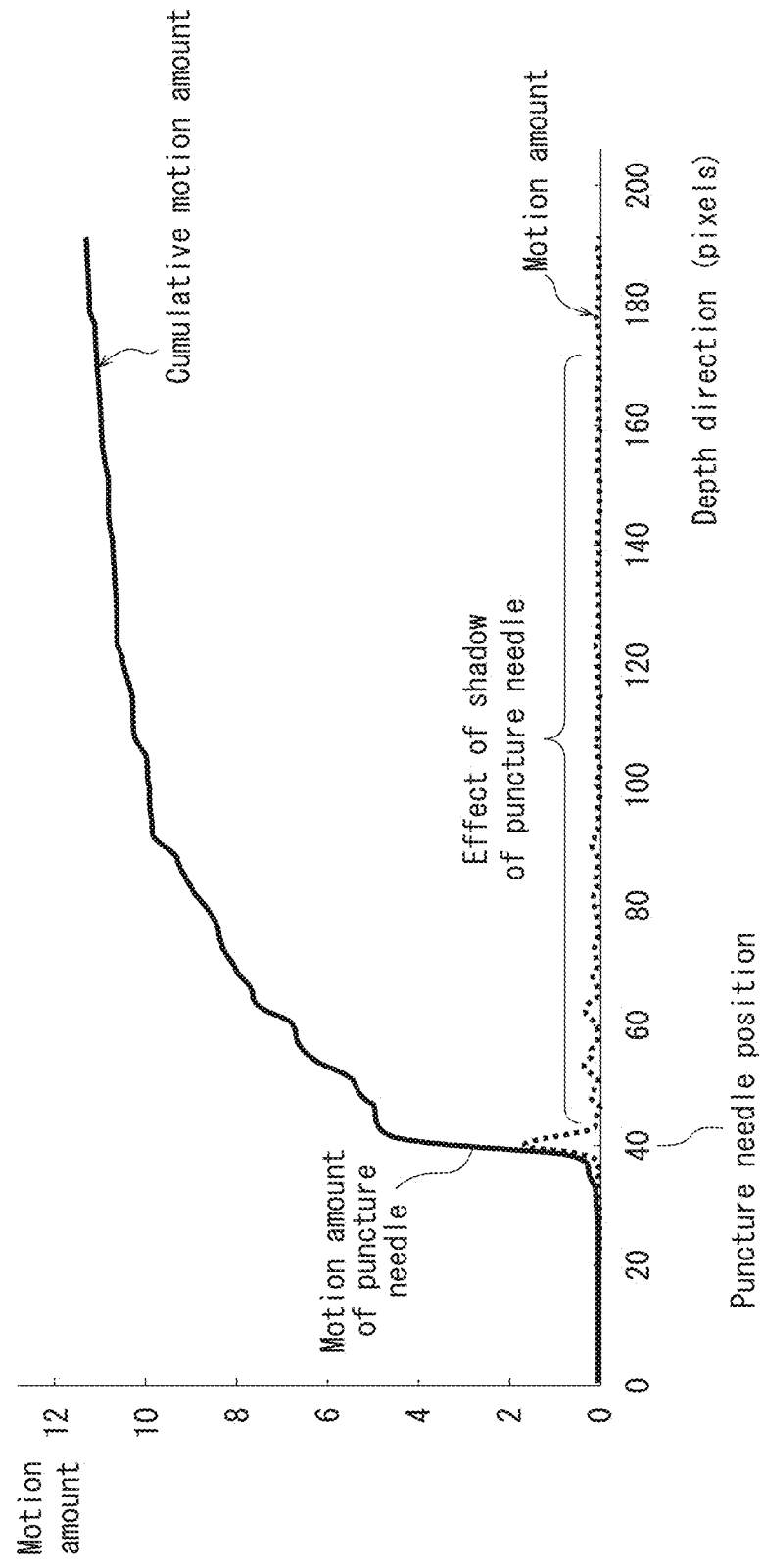
FIG. 4 is a graph of measured results indicating motion amounts and a cumulative motion amounts corresponding to the puncture needle in a depth direction according to the ultrasound diagnostic device 10 pertaining to embodiment 1.

Next, in a B-mode image signal acquired when inserting a puncture needle into a subject, distribution of the motion amount and a cumulative motion amount in the depth direction of an acoustic line signal is examined. FIG. 4 includes a measurement result indicating the motion amount and the cumulative motion amount of the puncture needle in the depth direction according to the ultrasound diagnostic device 10. As shown in FIG. 4, the motion amount (dashed line) has a peak when the puncture needle is at a certain depth (near pixel 40), and is also distributed in a range deeper than the puncture needle (from pixel 40 to the vicinity of pixel 180). The distribution of the motion amount in a range deeper than the puncture needle is due to the effect of the shadow of the puncture needle. As described above, a portion that newly becomes a shadow region of the puncture needle along with insertion of the puncture needle, i.e. insufficiently irradiated by the ultrasound beam, is recognized as having a motion amount according to a change in luminance because luminance is recognized as having changed when compared to a previous frame.

Distribution of a cumulative motion amount (solid line) is obtained by integrating the distribution of the motion amount in the depth direction. The cumulative motion amount has a distribution of abruptly increasing at the depth of the puncture needle (near pixel 40), increasing moderately at depths greater than pixel 40, and gradually increasing until near pixel 120 after which the cumulative motion amount is saturated. Further, according to the inventors' experiments, the amount of increase in the cumulative motion amount at the depth of the puncture needle remained substantially constant even when the depth of the puncture needle was changed. The reason for this is that the puncture needle has a smooth metal surface and a thickness limited to a prescribed range by criteria for use, and therefore when the puncture needle is inserted into the subject, the change in luminance and the motion amount indicated by the change in luminance in a B-mode image signal is constant. Accordingly, depth of the puncture needle can be correctly detected by detecting a rapid increase in the cumulative motion amount.

Figure 5:
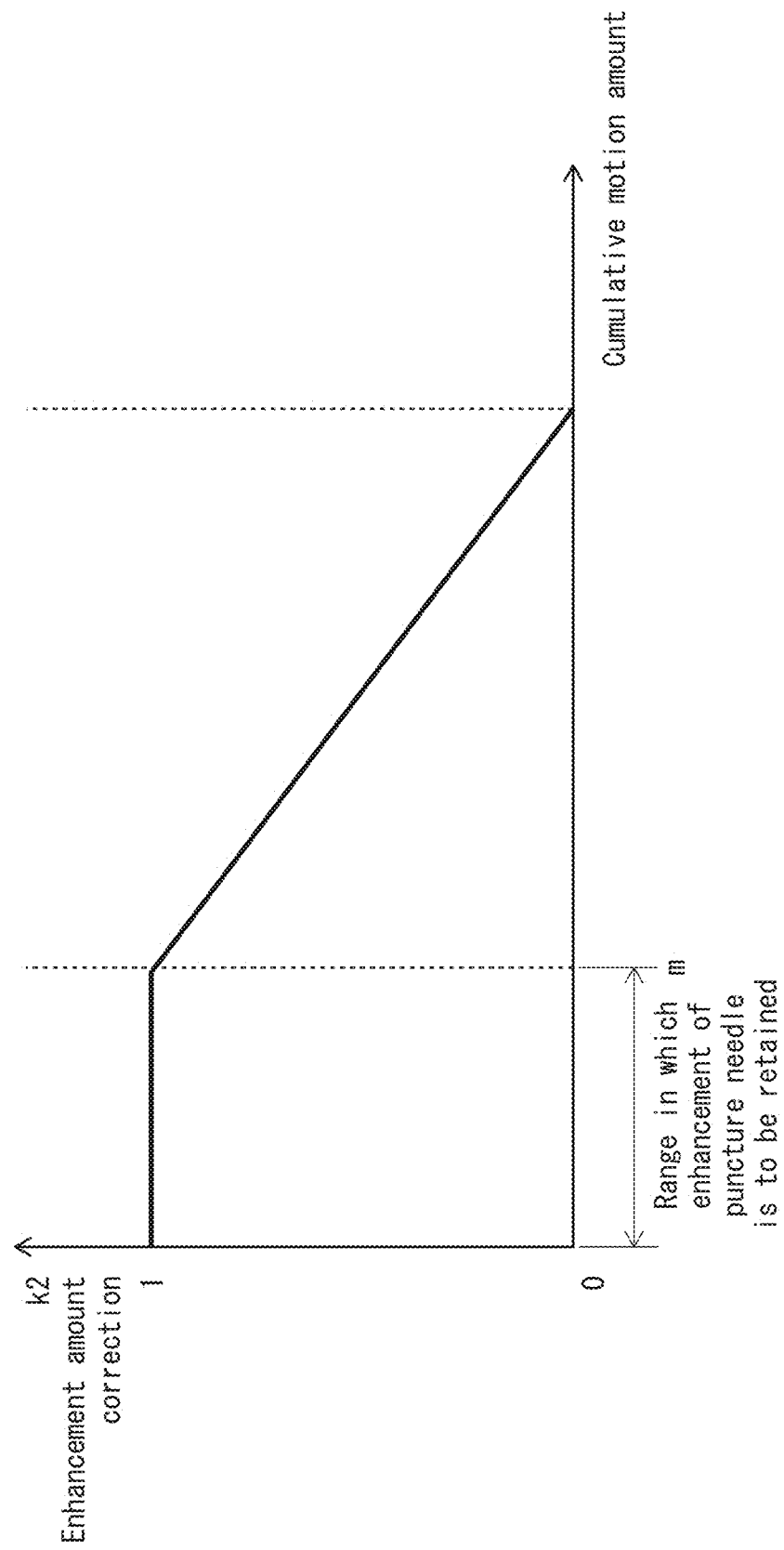
FIG. 5 is a graph indicating a relationship between input and output in an enhancement correction calculator 65 of the ultrasound diagnostic device 10 pertaining to embodiment 1.

FIG. 5 is a graph indicating a relationship between the cumulative motion amount, which is input, and an enhancement amount correction k2, which is output, in the enhancement correction calculator 65 of the ultrasound diagnostic device 10. As shown in FIG. 5, the enhancement amount correction k2 is a variable in a range from 0 to 1, and a predefined reference value m is a range of the cumulative motion amount in which enhancement of the puncture needle is preferably maintained. In the present embodiment, the enhancement amount correction k2 is 1 in a range from zero until the cumulative motion amount is the predefined reference value m, and decreases towards 0 after the cumulative motion amount exceeds the predefined reference value m. The predefined reference value m of the cumulative motion amount can be determined from the experimental results of FIG. 4, etc. For example, the predefined reference value m is preferably a cumulative motion amount slightly above a value after the abrupt increase at the depth of the puncture needle (near pixel 40 in FIG. 4). In the present embodiment, the predefined reference value m is preferably a value including a range from 6 to 10, and more preferably including a range from 6 to 8.

In this way, the enhancement amount (k1×k2) increases in proportion to the motion amount of the pixel region to be corrected, and when the cumulative motion amount of the pixel region to be corrected exceeds the predefined reference value, the enhancement amount is reduced in proportion to the amount of excess.

Figure 6:
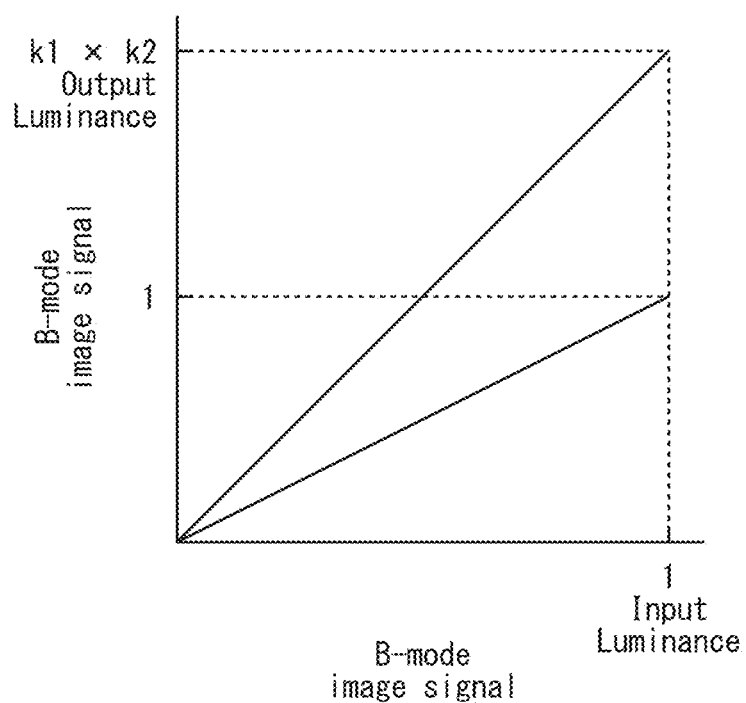
FIG. 6 is a graph indicating a relationship between input luminance and output luminance of a B-mode image signal in a B-mode image enhancer 63 of the ultrasound diagnostic device 10 pertaining to embodiment 1.

FIG. 6 is a graph indicating a relationship between input luminance and output luminance of a B-mode image signal in the B-mode image enhancer 63 of the ultrasound diagnostic device 10. In the enhancement processing for the B-mode image signal in the present embodiment, the input signal is increased and outputted based on the enhancement amount (k1×k2).

Figure 7:
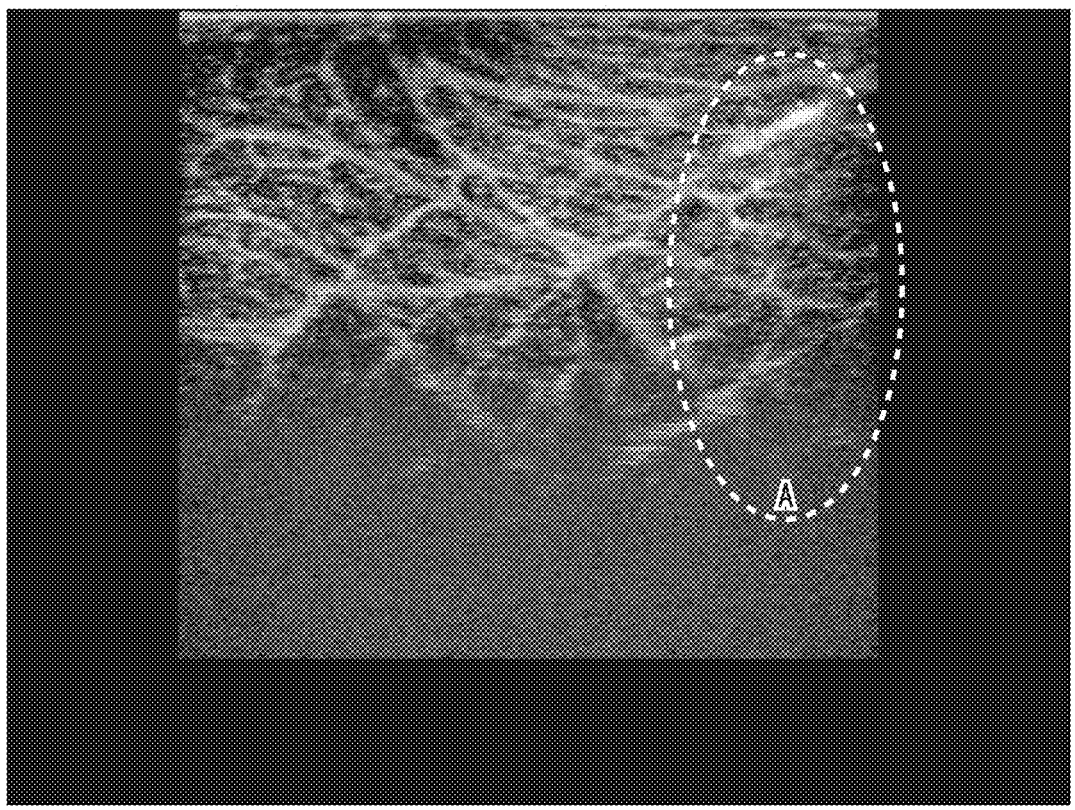
FIG. 7 is a B-mode image acquired by the ultrasound diagnostic device 10 pertaining to embodiment 1.
Figure 8:
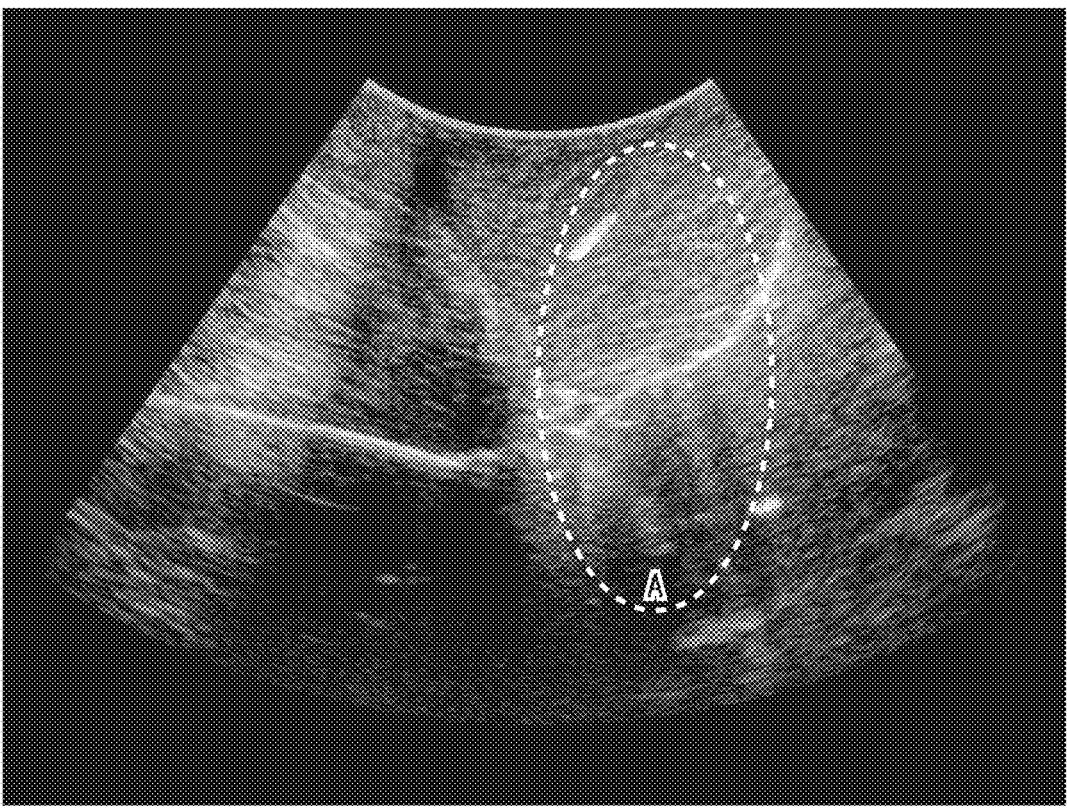
FIG. 8 is a B-mode image acquired by the ultrasound diagnostic device 10 pertaining to embodiment 1.

The following is an evaluation regarding the effect of preventing pseudo-enhancement in puncture needle enhancement processing in the ultrasound diagnostic device 10, by display of B-mode images. FIG. 7 and FIG. 8 are B-mode images acquired by the ultrasound diagnostic device 10. In FIG. 7 and FIG. 8, in each region A surrounded by a dashed line, the white portion in an upper portion of the region A is a display image of a puncture needle that has been enhanced. It can be seen that the puncture needle is enhanced in the same way as in the B-mode image acquired by the ultrasound diagnostic device 10X in FIG. 15. On the other hand, it can be seen that a portion colored white below the display image of the puncture needle in each region A is reduced and less conspicuous compared to FIG. 15. The white-colored portion visible in FIG. 15 is the shadow of the puncture needle that has been pseudo-enhanced, and is noise accompanying the puncture needle enhancement processing. In this way, it can be seen that, in the ultrasound diagnostic device 10, pseudo-enhancement of the puncture needle shadow that accompanies the puncture needle enhancement processing is reduced by adopting the above configuration.

Summary

As described above, in the ultrasound image processing method and the ultrasound diagnostic device using the ultrasound image processing method pertaining to embodiment 1, pseudo-enhancement with respect to the puncture needle is reduced by the configuration described above. Thus, visibility of the puncture needle is improved in ultrasound image diagnosis, prevention of image quality deterioration due to effects of the puncture needle is possible, and ease of use of the ultrasound diagnostic device is improved.

Embodiment 2

In the ultrasound diagnostic device 10 pertaining to embodiment 1, the cumulative motion calculator 64 calculates a cumulative motion amount of a target pixel region by cumulating motion amounts for each pixel region along a straight line parallel to the first direction that passes through the target pixel region from a pixel region located at an upstream end of the ultrasound beam to the target pixel region; and calculates a cumulative motion amount of each pixel region by performing this cumulating for each pixel region included in the current frame B-mode image signal. However, the cumulative motion calculator 64 may calculate a cumulative motion amount of each pixel region included in the current frame B-mode image signal by cumulating motion amounts for each pixel region substantially along a direction of transmission of the ultrasound beam from a pixel region at an upstream end of the ultrasound beam to the location of the target pixel region; and configuration of the cumulative motion calculator 64 can be changed appropriately.

In embodiment 2, the cumulative motion calculator 64 specifies, for each linear sequence of pixel regions in a second direction perpendicular to the first direction, a greatest motion amount among motion amounts corresponding to pixel regions in the linear sequence, and calculates the cumulative motion amount of a target pixel region by cumulating the greatest motion amounts from a pixel region located at the upstream end of the ultrasound beam to a location of the target pixel region along the first direction; and performs this calculation specifying each pixel region included in the present frame B-mode image signal as the target pixel region. Configuration other than the cumulative motion calculator 64 is the same for each element indicated in embodiment 1, and description thereof is omitted here.

Configuration

The following describes the ultrasound diagnostic device pertaining to embodiment 2, with reference to the drawings.

Figure 9:
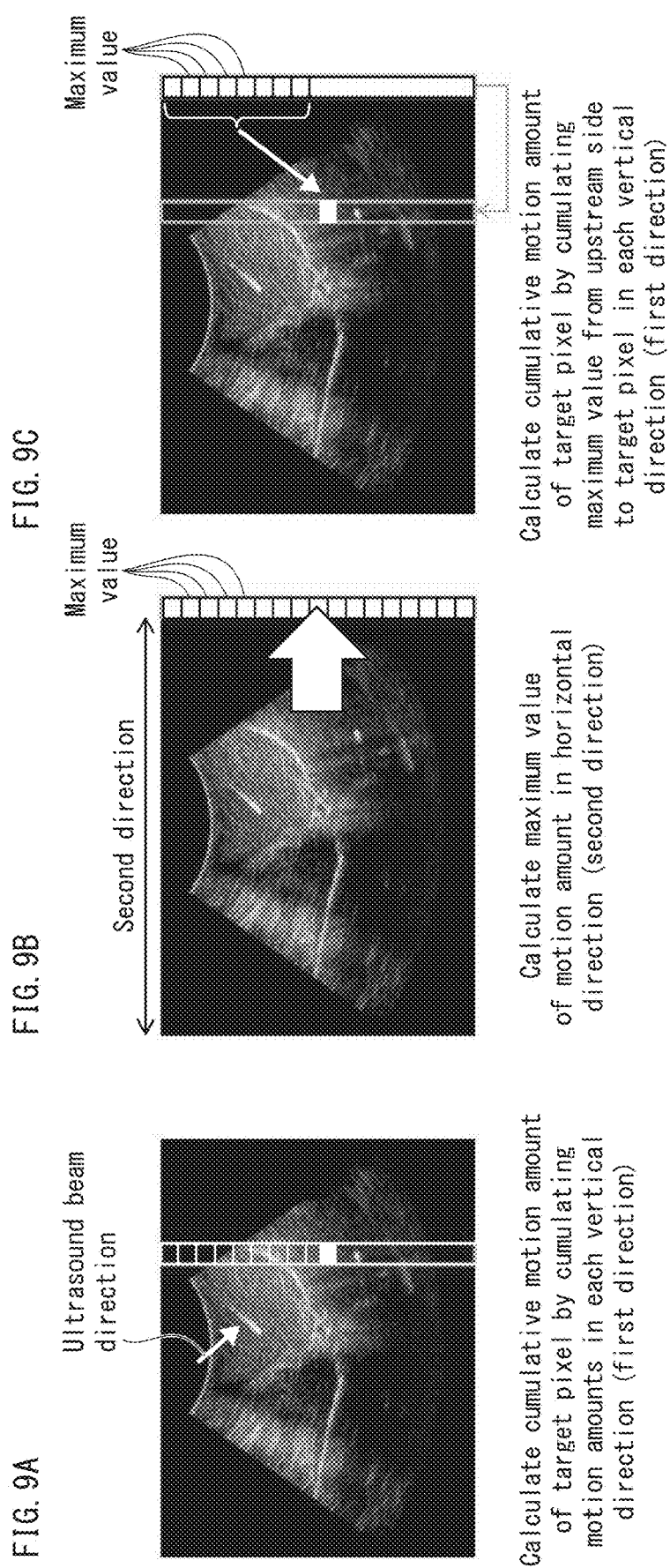
FIGS. 9A, 9B, and 9C are schematic diagrams for describing operation of a cumulative motion calculator 64 in an ultrasound diagnostic device pertaining to embodiment 2.

FIGS. 9A, 9B, and 9C are schematic diagrams for describing configuration of the cumulative motion calculator 64 in the ultrasound diagnostic device pertaining to embodiment 2.

FIG. 9A is a schematic diagram indicating configuration of the cumulative motion calculator 64 pertaining to embodiment 1. As indicated in the present diagram, in embodiment 1, the cumulative motion amount of a target pixel region is calculated by cumulating motion amounts from a pixel region located at the upstream end of the ultrasound beam in the first direction to the target pixel region. Thus, in a case in which, in the frame B-mode image signal, the ultrasound beam transmit direction and the first direction are not parallel and form a constant angle therebetween, the cumulative motion amount is reduced at a location removed from below the first direction of the puncture needle, and the enhancement amount correction is reduced with respect to the location.

Accordingly, a problem occurs in that a portion of the shadow region that occurs in the downstream side of the ultrasound beam transmit direction of the puncture needle protrudes from the portion below the first direction from the puncture needle, and the protruding portion becomes pseudo-enhanced. In FIG. 9A, the white speckling located in the bottom right of the fan-shaped image is a remaining portion of pseudo-enhancement.

Further, even when the beam transmit direction and the first direction are parallel on the frame B-mode image signal, in a case in which the ultrasound beam is a beam having a shape that spreads outward, a portion of the shadow region of the puncture needle that occurs downstream in the ultrasound beam transmit direction may protrude from the region below the first direction from the puncture needle in the B-mode image signal, causing the same problem.

On the other hand, FIG. 9B and FIG. 9C are schematic diagrams indicating a configuration of the cumulative motion calculator 64 pertaining to embodiment 2. As shown in the present diagram, in embodiment 2, in locations of each vertical direction (the first direction), the maximum value of the motion amount of each pixel region in the horizontal direction (the second direction) is calculated (FIG. 9B). Subsequently, the cumulative motion amount of a target pixel region is calculated by cumulating the maximum motion amounts from pixel regions located at the upstream end of the ultrasound beam in the first direction to the target pixel region (FIG. 9C). This processing calculates a cumulative motion amount of each pixel region by performing this cumulating for each pixel region included in the current frame B-mode image signal.

In this way, the cumulative motion amount along the first direction is a cumulated amount of the maximum value of motion amounts in each first direction location in the second direction. Thus, even in a case in which a portion of the shadow region of the puncture needle that occurs downstream of the ultrasound beam transmit direction is located apart from the first direction below the puncture needle, the cumulative motion amount of the portion of the shadow region becomes the same value as when below the puncture needle in the first direction. Accordingly, in the shadow region of the puncture needle that occurs downstream of the ultrasound beam transmit direction, pseudo-enhancement of a portion protruding from the first direction below the puncture needle can be prevented.

<Operation>

Figure 10:
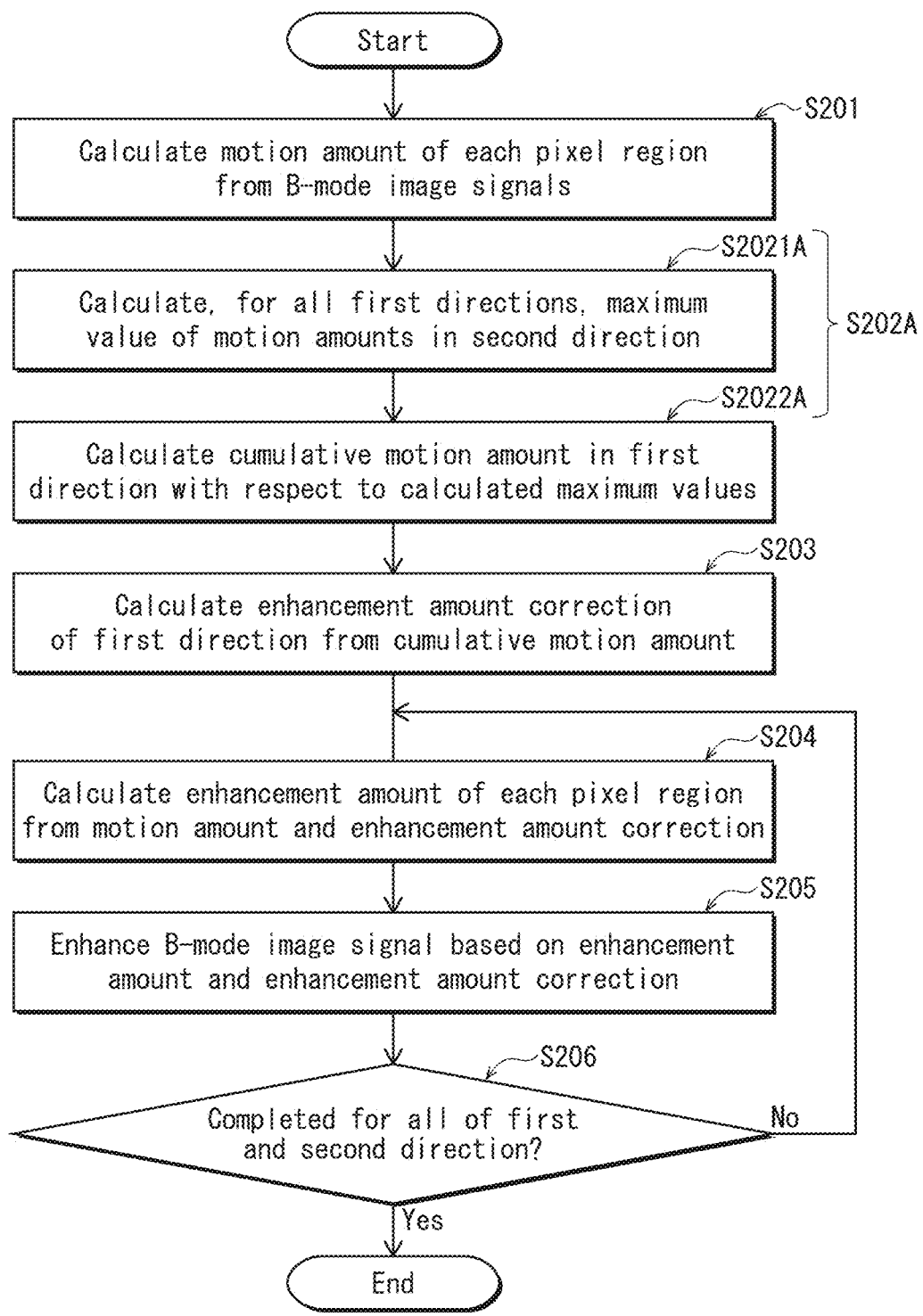
FIG. 10 is a flowchart indicating operation of an enhancement processor 6A in the ultrasound diagnostic device pertaining to embodiment 2.

FIG. 10 is a flowchart indicating operation of the enhancement processor 6 in the ultrasound diagnostic device pertaining to embodiment 2.

1. Step S201

Step S201 is identical to embodiment 1. The motion amount of an object in a frame B-mode image signal is calculated from an inter-frame difference of a plurality of frame B-mode image signals.

2. Step S202A

Step S202A has a sub-step S2021A and a sub-step S2022A.

In the sub-step S2021A, the cumulative motion calculator 64 calculates a motion amount of a pixel region that has the greatest motion amount among pixel regions in the second direction perpendicular to the first direction as a maximum motion amount of the second direction.

In sub-step S2022A, the cumulative motion calculator 64 calculates the cumulative motion amount of a target pixel region by cumulating the maximum motion amount of the second direction from a pixel region location at the upstream end of the ultrasound beam along the first direction to the target pixel region. This processing calculates a cumulative motion amount of each pixel region by performing this cumulating for all pixel regions included in the current frame B-mode image signal.

3. Step S203

Step S203 is identical to embodiment 1. The enhancement correction calculator 65 calculates an enhancement amount correction for each pixel region, based on the cumulative motion amount of each pixel region of a frame B-mode image signal.

4. Step S204

Step S204 is identical to embodiment 1. The enhancement calculator 62 calculates an enhancement amount for each pixel of the frame B-mode image signal, based on the motion amount of each pixel region supplied from the motion calculator 61 and the enhancement amount correction for each pixel region supplied from the enhancement correction calculator 65.

5. Step S205

The B-mode image enhancer 63 is identical in embodiment 1. The B-mode image enhancer 63 performs enhancement processing with respect to the B-mode image signal unit of each pixel region of the frame B-mode image signal, based on the frame B-mode image signal supplied from the B-mode image acquirer 5 and the enhancement amount for each pixel region of the frame B-mode image signal supplied from the enhancement calculator 62. The frame B-mode image signal that has been enhanced is generated, and outputted to the display 8 via the display controller 7.

Effect of Preventing Pseudo-Enhancement

Figure 11:
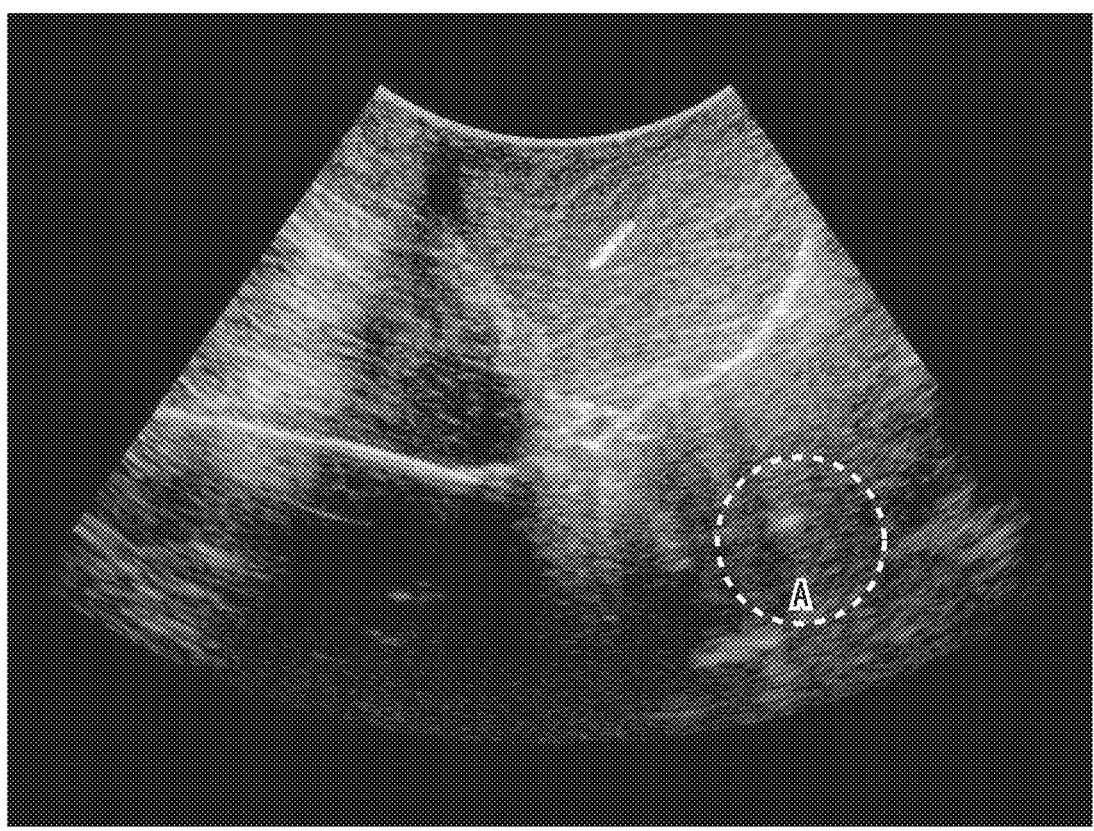
FIG. 11 is a B-mode image in which a puncture needle has been enhanced, acquired by the ultrasound diagnostic device pertaining to embodiment 2.

The following is an evaluation of the effect of preventing pseudo-enhancement in embodiment 2 from a B-mode image. FIG. 11 is a B-mode image acquired by the ultrasound diagnostic device pertaining to embodiment 2. FIG. 8 is a B-mode image acquired by the ultrasound diagnostic device 10 pertaining to embodiment 1. In FIG. 8, the white speckled location near the lower-right of region A surrounded by a broken line is a portion of a shadow region of the puncture needle that occurs downstream in the ultrasound beam transmit direction, which protrudes from a location below the puncture needle in the first direction on the B-mode image and has been pseudo-enhanced. In contrast, in FIG. 11, the white speckled location in region A surrounded by a broken line is less intense and no longer conspicuous. In other words, in the configuration pertaining to embodiment 2, in the shadow region that occurs downstream of the puncture needle in the ultrasound beam transmit direction, enhancement correction is performed based on a cumulative motion amount with respect to a portion protruding from below the first direction of the puncture needle, and the pseudo-enhancement that occurs in embodiment 1 is noticeably reduced.

Summary

As described above, in the ultrasound image processing method and the ultrasound diagnostic device using the ultrasound image processing method pertaining to embodiment 2, the following effect is achieved in addition to the effect in embodiment 1.

In a case in which the ultrasound beam transmit direction and the first direction are not parallel and form a constant angle on the frame B-mode image signal, a problem occurs in that a portion of the shadow region that occurs in the downstream side of the ultrasound beam transmit direction of the puncture needle protrudes from the portion below the first direction from the puncture needle in the B-mode image signal, and the protruding portion becomes pseudo-enhanced. In a case in which the ultrasound beam is a beam having a shape that spreads outward, the same problem also occurs.

However, in embodiment 2, according to the above configuration, the enhancement amount correction is calculated based on the cumulative motion amount even for a protruding portion as described above, reducing the pseudo-enhancement that occurs in embodiment 1.

Embodiment 3

In embodiment 1, a frame B-mode image signal is enhanced by calculating an enhancement amount for a B-mode image signal of a pixel region, based on motion amounts calculated from B-mode image signals of pixel regions included in a plurality of frame B-mode image signals.

However, enhancement processing may be performed with respect to a plurality of frame receive signals by calculating an enhancement amount for a receive signal unit corresponding to a pixel region, based on a characteristic calculated from receive signal units of pixel regions included in a plurality of frame receive signals, and a target of enhancement processing may be changed appropriately.

An ultrasound diagnostic device 10A pertaining to embodiment 3 is characterized in that an enhancement amount with respect to an acoustic line signal unit corresponding to a pixel region is calculated based on a motion amount calculated from an acoustic line signal unit corresponding to a pixel region composed of at least one pixel included in acoustic line signals of a plurality of frames, and enhancement processing is performed with respect to the acoustic line signal units of a frame.

Configuration

Figure 12:
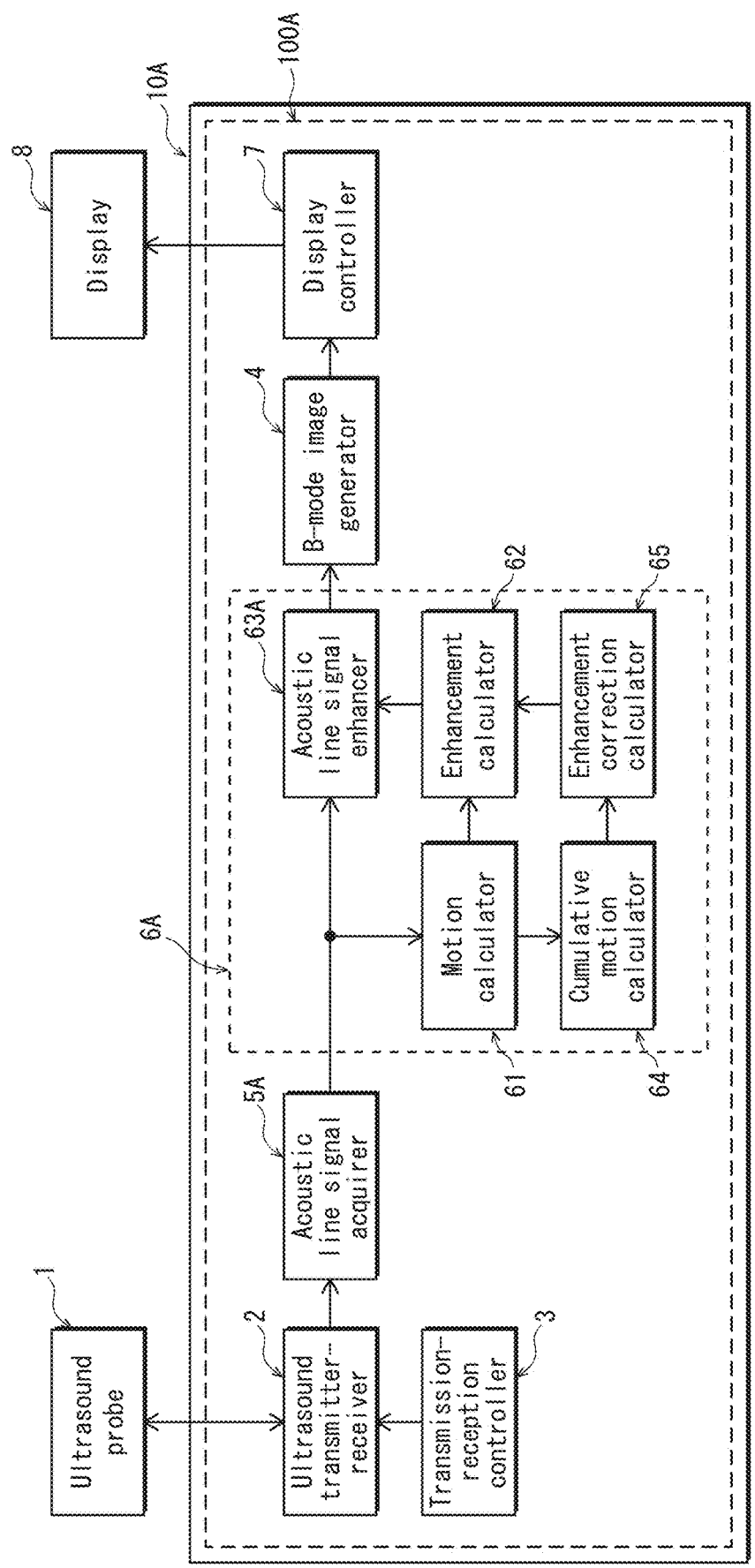
FIG. 12 is a function block diagram of an ultrasound diagnostic device 10A pertaining to embodiment 3.

The following describes configuration of the ultrasound diagnostic device 10A. FIG. 12 is a function block diagram of the ultrasound diagnostic device 10A pertaining to embodiment 3. The ultrasound diagnostic device 10A includes a control circuit 100A provided with the ultrasound transmitter-receiver 2, the transmission-reception controller 3, the B-mode image generator 4, an acoustic line signal acquirer 5A, an enhancement processor 6A, and the display controller 7. Configuration other than the acoustic line signal acquirer 5A and the enhancement processor 6A is the same for each element indicated in embodiment 1, and description thereof is omitted here.

1. Acoustic Line Signal Acquirer 5A

The acoustic line signal acquirer 5A is a circuit provided with a buffer storing frame acoustic line signals sequentially transmitted as scanning is performed, as inputs of acoustic line signals generated at the ultrasound transmitter-receiver 2. The frame acoustic line signals are outputted to the enhancement processor 6A.

2. Enhancement Processor 6A

The enhancement processor 6A includes the motion calculator 61, the enhancement calculator 62, the cumulative motion calculator 64, an enhancement correction calculator 65, and an acoustic line signal enhancer 63A. Configuration other than the acoustic line signal enhancer 63A is identical to embodiment 1, and description thereof is omitted here. Further, according to the acoustic line signal enhancer 63A, the acoustic line signal replaces the B-mode image as a target for enhancement processing, but is otherwise identical to the B-mode image enhancer 63.

The acoustic line signal enhancer 63A is a circuit that performs enhancement processing on the acoustic line signal unit of each pixel region of a frame acoustic line signal, acquiring the frame acoustic line signal from the acoustic line signal acquirer 5A and an enhancement amount for each pixel region of the frame acoustic line signal from the enhancement calculator 62. The acoustic line signal enhancer 63A outputs the frame acoustic line signal that has been enhanced to the B-mode image generator 4. The frame acoustic line signal that has been enhanced is converted to a B-mode image signal and outputted to the display 8 via the display controller 7.

Enhancement processing in the ultrasound diagnostic device 10A is identical to the flowchart in FIG. 2, except that the B-mode image signal is replaced by the acoustic line signal.

Summary

As described above, the ultrasound diagnostic device 10A achieves the following effects in addition to the effects of the ultrasound diagnostic device 10 indicated in embodiment 1.

In the ultrasound diagnostic device 10A, enhancement amounts of pixel regions are generated based on characteristic values calculated from the acoustic line signal units corresponding to pixel regions included in the acoustic line signals of a plurality of frames. In this way, by performing enhancement processing on acoustic line signals instead of B-mode image signals, the influence of operator-specific image quality adjustments included when generating a B-mode image is eliminated and enhancement amounts are determined with respect to the puncture needle at the acoustic line signal stage. Thus, enhancement amounts are determined independent of operator-specific adjustments.

Further, as described above, in a case in which the ultrasound beam transmit direction and the first direction are not parallel and form a constant angle on the frame B-mode image signal, a problem occurs in that a portion of the shadow region that occurs in the downstream side of the ultrasound beam transmit direction of the puncture needle protrudes from the region below the first direction from the puncture needle in the B-mode image signal, and the protruding region becomes pseudo-enhanced. In embodiment 3, according to the above configuration, the first direction used to calculate the cumulative motion amount is the direction of the acoustic line signal, and therefore the first direction and the ultrasound beam transmit direction are always parallel. Thus, protruding portions do not exist, and the problem of pseudo-enhancement of the protruding portions does not occur. Thus, even when using an identical processing method to embodiment 1, pseudo-enhancement is eliminated.

Other Modifications

The above describes ultrasound diagnostic devices pertaining to each embodiment. The present invention is not limited to the above embodiments and may be appropriately modified based on aspects of implementation.

In the above embodiments, the B-mode image enhancer 63 performs enhancement processing for the B-mode image signal to increase luminance indicated by a receive signal unit corresponding to a target pixel region by an amount proportional to the enhancement amount. However, display of an enhancement amount is not limited in this way, and may be appropriately modified. For example, the B-mode image enhancer 63 may be configured to perform enhancement processing with respect to the B-mode image signal so that color displayed on the display is changed based on a receive signal unit corresponding to a target pixel region based on the enhancement amount. Further, the B-mode image enhancer 63 may be configured to sequentially perform enhancement processing with respect to the B-mode image signals so that enhancement effect duration is increased for a receive signal unit corresponding to a target pixel region in proportion to an increase in enhancement amount. In this way, enhancement effect can be represented more prominently.

Further, in the above embodiments, the ultrasound probe is indicated to be an ultrasound probe in which a plurality of piezoelectric elements are arranged in a one-dimensional direction. However, configuration of the ultrasound probe is not limited in this way. For example, an ultrasound probe may be used in which a plurality of piezoelectric elements are arranged in two dimensions. In a case in which an ultrasound probe having a two-dimensional arrangement is used, irradiation position and irradiation direction of a transmitted ultrasound beam can be controlled according to changes in timing of voltage and voltage values applied individually to piezoelectric elements.

Further, the ultrasound probe may include a portion of functions of the transmitter-receiver. For example, based on a control signal for generating a transmit electrical signal outputted from the transmitter-receiver, the ultrasound probe may generate the transmit electrical signal internally, and convert the transmit electrical signal to ultrasound. In addition, a configuration can be adopted that can convert a received reflected ultrasound to a receive electrical signal and generate a receive signal based on the receive electrical signal in the ultrasound probe.

Further, each processing unit included in the ultrasound diagnostic device pertaining to each embodiment is typically implemented as an LSI, which is an integrated circuit. Each processing unit, a portion of a processing unit or all processing units may be a single chip.

Further, in the embodiments, each block is described as independent hardware. However, each block in the ultrasound diagnostic device need not be independent hardware. For example, functions of each block may be implemented by a CPU or software as required.

Further, a portion of functions or all functions of each function block of the ultrasound diagnostic device is typically implemented as an LSI, which is an integrated circuit. Each function block, a portion of a function block or all function blocks may be a single chip. Note that LSI may be referred to as IC, system LSI, super LSI, or ultra LSI, depending on the degree of integration.

Note that methods of integration are not limited to LSI, and may be implemented by dedicated circuits or general-purpose processors. After LSI manufacture, a field programmable gate array (FPGA) that allows programming or a re-configurable processor that allows re-configuring of connections and settings of circuit cells within the LSI may be used.

Further, if integrated circuit technology that replaces LSI is introduced due to progress of semiconductor technology or derivative technology, integration of function blocks is of course possible using the technology.

Further, a portion or all functions of the ultrasound diagnostic device pertaining to each embodiment may be implemented by execution of a program by a processor such as a CPU.

Furthermore, the present invention may be the program described above, or may be a non-transitory computer-readable storage medium storing the program described above. Further, the program described above may of course be distributed by a transmission medium such as the internet.

Further, divisions of functional blocks in the block diagrams are examples, and a plurality of function blocks may be implemented as a single function block, a single function block may be divided into a plurality of function blocks, and a portion of functions may be moved to another function block. Further, functions of a plurality of function blocks having similar functions may be processed in parallel or by time division by a single piece of hardware or software.

Further, orders in which the above steps are implemented are merely examples for describing specifics of the present invention, and orders other than the orders described above may be used. Further, a portion of a step described above may be executed at the same time as another step.

Further, at least a portion of functions of the ultrasound diagnostic device pertaining to each embodiment or modification may be combined.

Further, various modifications to the present embodiments within a range that occurs to those skilled in the art are also included in the present invention.

Summary

As described above, the ultrasound image processing method pertaining to the present embodiment is an ultrasound image processing method for correcting at least one of a plurality of frame receive signals generated based on ultrasound scans performed sequentially, an ultrasound probe transmitting an ultrasound beam towards a range to be scanned in a subject and receiving reflected ultrasound in each of the ultrasound scans, the ultrasound image processing method comprising: acquiring at least two of the frame receive signals; calculating motion amounts, each indicating motion of an object in the subject and corresponding to a respective one of a plurality of pixel regions in one of the two frame receive signals, each of the pixel regions indicating a region of at least one pixel, the calculating of each of the motion amounts being performed based on receive signal units corresponding to identical pixel regions included in the at least two of the frame receive signals (S201); calculating cumulative motion amounts, each corresponding to a target pixel region in the one frame receive signal, by cumulating motion amounts corresponding to reference pixel regions in the one frame receive signal that are located substantially along a direction of transmission of the ultrasound beam from a pixel region located at an upstream end of the ultrasound beam to the target pixel region, each of the pixel regions included in the one frame receive signal being specified as the target pixel region (S202); calculating enhancement amounts for receive signal units, each of the receive signal units corresponding to a respective one of the pixel regions included in the one frame receive signal, the enhancement amounts being based on the motion amounts and the cumulative motion amounts (S204); and enhancing the receive signal units based on the enhancement amounts (S205).

Further, the ultrasound diagnostic device 10 pertaining to the present embodiment is an ultrasound diagnostic device for correcting at least one of a plurality of frame receive signals generated based on ultrasound scans performed sequentially, an ultrasound probe transmitting an ultrasound beam towards a range to be scanned in a subject and receiving reflected ultrasound in each of the ultrasound scans, the ultrasound diagnostic device 10 comprising: a control circuit 100, the control circuit comprising: a receive signal acquirer that acquires at least two of the frame receive signals; the motion calculator 61 that calculates motion amounts, each indicating motion of an object in the subject and corresponding to a respective one of a plurality of pixel regions in one of the two frame receive signals, each of the pixel regions indicating a region of at least one pixel, the calculating of each of the motion amounts being performed based on receive signal units corresponding to identical pixel regions included in the at least two of the frame receive signals; the cumulative motion calculator 64 that calculates cumulative motion amounts, each corresponding to a target pixel region in the one frame receive signal, by cumulating motion amounts corresponding to reference pixel regions in the one frame receive signal that are located substantially along a direction of transmission of the ultrasound beam from a pixel region located at an upstream end of the ultrasound beam to the target pixel region, each of the pixel regions included in the one frame receive signal being specified as the target pixel region; the enhancement calculator 62 that calculates enhancement amounts for receive signal units, each of the receive signal units corresponding to a respective one of the pixel regions included in the one frame receive signal, the enhancement amounts being based on the motion amounts and the cumulative motion amounts; and the receive signal enhancer 63 that enhances the receive signal units based on the enhancement amounts.

Further, when the direction is a first direction, the reference pixel regions may be located along a straight line parallel to the first direction from a pixel region located at the upstream end of the ultrasound beam to the target pixel region.

Further, when a second direction is perpendicular to the direction, each of the reference pixel regions may be a pixel region corresponding to a greatest motion amount among motion amounts corresponding to pixel regions in a linear sequence in the second direction.

According to the ultrasound image processing method and the ultrasound diagnostic device using the ultrasound image processing method, pseudo-enhancement with respect to a puncture needle is reduced, and visibility of the puncture needle in ultrasound imaging is improved while preventing image quality deterioration caused by the puncture needle. Thus, ease of use of the ultrasound diagnostic device is improved.

<Supplement>

The embodiments described above each illustrate a preferred embodiment of the present invention. Values, shapes, materials, elements, positions and connections of elements, processes, process orders, etc., indicated in the embodiments are examples, and are not intended to limit the present invention. Further, among elements of the embodiments, a process not recited in independent claims that indicate the most significant concepts of the present invention is described as an element of a more preferred form.

Further, in order to make understanding of the invention easier, scale of each element of the above embodiments may differ from actual scale. Further, the present invention is not limited to the description of the above embodiments and may be modified as appropriate without departing from the spirit and scope of the present invention.

Further, members such as circuit components on a substrate, lead wires, etc., also exist in the ultrasound diagnostic device, but electrical wiring and electrical circuits may be implemented various ways based on ordinary skill in the art, and are not described as they do not have direct relevance to description of the present invention. Note that each drawing indicated above is a schematic diagram, and the present invention is not necessarily exactly as shown.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. An ultrasound image processing method for correcting at least one of a plurality of frame receive signals generated based on ultrasound scans performed sequentially, an ultrasound probe transmitting an ultrasound beam towards a scanning range to be scanned in a subject and receiving reflected ultrasound in each of the ultrasound scans, the ultrasound image processing method comprising:

acquiring at least two of the plurality of frame receive signals, wherein a first frame receive signal of the at least two of the plurality of frame receive signals includes a plurality of first receive signal units each corresponding to a respective one of a plurality of pixel regions in the first frame receive signal, and a second frame receive signal of the at least two of the plurality of frame receive signals includes a plurality of second receive signal units each corresponding to a respective one of a plurality of pixel regions in the second frame receive signal, wherein each of the plurality of pixel regions in the first frame receive signal and each of the plurality of pixel regions in the second frame receive signal indicate a region of at least one pixel;

calculating motion amounts, each indicating motion of an object in the subject and corresponding to a respective one of the plurality of pixel regions in the first frame receive signal, the calculating of each of the motion amounts being performed based on respective pairs of the first and second receive signal units corresponding to identical pixel regions included respectively in the first frame receive signal and the second frame receive signal;

calculating cumulative motion amounts, each corresponding to a target pixel region in the first frame receive signal, by cumulating motion amounts corresponding to reference pixel regions in the first frame receive signal that are located between an upstream end of the ultrasound beam and the target pixel region with respect to a first direction that is substantially parallel to a direction of transmission of the ultrasound beam, each of the plurality of pixel regions included in the first frame receive signal being specified as the target pixel region;

calculating enhancement amounts for the first receive signal units, each of the first receive signal units corresponding to a respective one of the plurality of pixel regions included in the first frame receive signal, the enhancement amounts being based on the motion amounts and the cumulative motion amounts, wherein the enhancement amounts are increased in proportion to the motion amounts, and calculating the enhancement amounts further comprises comparing the cumulative motion amounts of the plurality of pixel regions included in the first frame receive signal with a predefined reference value which is stored in advance, and, when a given one of the cumulative motion amounts exceeds the predefined reference value which is stored in advance, decreasing the enhancement amount of the one of the plurality of pixel regions included in the first frame receive signal corresponding to the given one of the cumulative motion amounts that exceeds the predefined reference value, in proportion to an amount by which the given one of the cumulative motion amounts exceeds the predefined reference value;

enhancing the first receive signal units based on the corresponding calculated enhancement amounts; and generating an enhanced ultrasound image based on the enhanced first receive signal units.

2. The ultrasound image processing method of claim 1, wherein the reference pixel regions are located along a straight line parallel to the first direction from a pixel region located at the upstream end of the ultrasound beam to the target pixel region.

3. The ultrasound image processing method of claim 1, wherein each of the reference pixel regions is a pixel region between the upstream end of the ultrasound beam and the target region with respect to the first direction, and corresponding to a greatest motion amount among motion amounts corresponding to pixel regions arranged in a linear sequence in a second direction that is perpendicular to the first direction.

4. The ultrasound image processing method of claim 1, wherein the reference pixel regions are located along the direction of transmission of the ultrasound beam.

5. The ultrasound image processing method of claim 1, wherein the motion amounts are determined based on differences between luminance indicated by the first receive signal units in the first frame receive signal and luminance indicated by the second receive signal units corresponding to identical pixel regions in the second frame receive signal, wherein the second frame receive signal is generated based on an ultrasound scan prior to an ultrasound scan corresponding to the first frame receive signal, and the motion amount of a given one of the plurality of pixel regions in the first frame receive signal is proportional to a size of the difference between the luminance indicated by the first receive signal unit corresponding to the given one of the plurality of pixel regions in the first frame receive signal and the luminance indicated by the second receive signal unit corresponding to a pixel region in the second frame receive signal that is identical to the given one of the plurality of pixel regions in the first frame receive signal.

6. The ultrasound image processing method of claim 1, wherein luminance indicated by the first receive signal units is increased in proportion to the enhancement amounts.

7. The ultrasound image processing method of claim 1, wherein color indicated by the first receive signal units is changed based on the enhancement amounts.

8. The ultrasound image processing method of claim 6, wherein enhancement effect duration with respect to the first receive signal units is increased in proportion to the enhancement amounts.

9. The ultrasound image processing method of claim 1, wherein a puncture needle is inserted within the scanning range in the subject, and the enhancement amounts are larger for first receive signal units among the first receive signal units of the first frame receive signal in which the puncture needle is indicated as compared to first receive signal units among the first receive signal units of the first frame receive signal in which the puncture needle is not indicated.

10. The ultrasound image processing method of claim 1, wherein the first frame receive signal is one of a frame B-mode image signal and a frame acoustic line signal.

11. A computer-readable non-transitory storage medium storing a program executable by a computer to perform the ultrasound image processing method of claim 1.

* * * * *